US007517858B1

(12) United States Patent
Hostetler et al.

(10) Patent No.: US 7,517,858 B1
(45) Date of Patent: Apr. 14, 2009

(54) PRODRUGS OF PHARMACEUTICALS WITH IMPROVED BIOAVAILABILITY

(75) Inventors: Karl Y. Hostetler, Del Mar, CA (US); Ganesh D. Kini, San Diego, CA (US); James R. Beadle, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 08/487,081

(22) Filed: Jun. 7, 1995

(51) Int. Cl.
*C07F 9/02* (2006.01)
(52) U.S. Cl. .............................. 514/23; 514/75; 514/80; 514/103
(58) Field of Classification Search .................. 514/23, 514/75, 80, 103
See application file for complete search history.

(56) References Cited

U.S. PATENT DOCUMENTS

| | | | |
|---|---|---|---|
| 4,215,113 A | 7/1980 | Eriksson et al. | |
| 4,339,445 A | 7/1982 | Eriksson et al. | |
| 4,386,081 A | 5/1983 | Helgstrand et al. | |
| 4,591,583 A | 5/1986 | Helgstrand et al. | |
| 4,619,794 A * | 10/1986 | Hauser ........................ | 264/4.1 |
| 4,665,062 A | 5/1987 | Eriksson et al. | |
| 4,771,041 A | 9/1988 | Eriksson et al. | |
| 5,072,032 A | 12/1991 | McKenna | |
| 5,194,654 A | 3/1993 | Hostetler et al. | |
| 5,223,263 A * | 6/1993 | Hostetler ..................... | 424/450 |
| 5,411,947 A * | 5/1995 | Hostetler et al. .............. | 514/43 |
| 5,436,234 A * | 7/1995 | Eibl ............................ | 514/77 |
| 5,463,092 A * | 10/1995 | Hostetler et al. .............. | 554/40 |
| 5,484,809 A * | 1/1996 | Hostetler et al. ............ | 514/449 |
| 5,484,911 A * | 1/1996 | Hong et al. .............. | 536/26.22 |
| 5,512,671 A | 4/1996 | Piantadosi et al. ......... | 536/26.1 |
| 5,827,831 A * | 10/1998 | Hostetler et al. .............. | 514/47 |

FOREIGN PATENT DOCUMENTS

| | | |
|---|---|---|
| AU | B-47082/93 | 8/1993 |
| DE | 42 26 279 | 8/1992 |
| JP | S59-273919 | 12/1984 |
| JP | 61-152694 * | 7/1986 |
| WO | PCT/US91/02447 | 4/1991 |

OTHER PUBLICATIONS

Takako et al., HCA abstract of JP 61-152694, Jul. 1986.*
Reman et al., Chem. Phys. Lipids 3 (1969) p. 221-223.*
Bangham, A.D. et al. (1965) Diffusion of univalent ions across the lamellae of swollen phospholipids. J. Mol. Biol. 13:238-252.
Berge, S. et al. (1977) Pharmaceutical salts. Journal of Pharmaceutical Sciences 66(1):1-19.
Bose, A. et al. (1973) A facile replacement of hydroxyl by halogen with inversion. Tetrahedron Letters 40:3937-3940.
Boina, et al. (1979) Izvesti i a akademii nauk SSSR. Seri i a Khimicheska 10:2362.
Cesarotti, E., et al. (1993) Synthesis and ruthenium-catalyzed enantioselective hydrogenation of 3-0-substituted 1,3-dihydroxypropan-2-ones. Helvetica Chimica Acta 76:2344-2349.
Chesebro, B. et al. (1988) Development of a sensitive quantitative focal assay for human immunodeficiency virus infectivity. Journal of Virology 62(10):3779-3788.
Chrisp, P. et al. (1991) Foscarnet: A review of its antiviral activity, pharmacokinetic properties and therapeutic use in immounocompromised patients with cytomegalovirus retinitis. Drugs 41(1):104-129.
Corey, E.J. et al. (1977) A direct total synthesis of thromboxane $B_2$ (=). Thetrahedron Letter 9:785-788.
Evans, D. et al. (1977) Thiosilanes, a promising class of reagents for selective carbonyl protection. Journal of the American Chemical Society 99:5009-5017.
Fukuzawa, A. et al. (1987) Synthesis of (=)-prepinnaterpene, a bromoditerpene from the red alga *Laurencia pinnata* yamada. Tetrahedron Letter 28(37):4303-4306.
Helgstrand, E. et al. (1978) Trisodium phosphonoformate, a new antiviral compound. Science 201:819-821.
Kern, E. (1990) Preclinical evaluation of antiviral agents: in vitro and animal model testing. Antiviral Agents and Viral Diseases of Man. 3rd edition; pp. 87-123.
Kim, et al. (1983) Preparation of multivesicular liposomes. Biochimica et Biophysica Acta 728:339-348.
Kluge, A. et al. (1972) Synthesis of prostaglandin models and prostaglandins by conjugate addition of a functionalized oganocopper reagent[1]. Journal of the American Chemical Society 94:7827-7832.
Kobayashi, Y. et al. (1968) Studies of organic fluorine compounds IV[1] conversion of alcohols to fluorides by diphenyltrifluorophosphorane. Chem. Pharm. Bull. 16:1784-1787.
Lambert, R. et al. (1989) Synthesis and antiviral activity of phosphonoacetic and phosphonoformic acid esters of 5-bromo-2'-deoxyuridine and related pyrimidine nucleosides and acyclonucleosides. American Chemical Society 32:367-374.
Larder, B. et al. (1989) HIV with reduced sensitivity to zidovudine (AZT) isolated during prolonged therapy. Reports 243:1731-1734.
Larder, B. et al. (1990) Susceptibilities of zidovudine-susceptible and -resistant human immunodeficiency virus isolates to antiviral agents determined by using a quantitative plaque reduction assay. Antimicrobial Agents and Chemotherapy 34(3):436-441.
Leserman, L. et al. (1980) Targeting to cells of fluorescent liposomes covalently coupled with monoclonal antibody or protein A. Nature 288:602-604.
Mayer, L. et al. (1986) Vesicles of variable sizes produced by a rapid extrusion procedure. Biochimica et biophysica Acta 858:161-168.
Mayhew, E. et al. (1984) Characterization of liposomes prepared using a microemulsifier. Biochimica et Biophysica Acta 775:169-174.
Norén, J. et al. (1983) Synthesis of esters of phosphonoformic acid and their antiherpes activity[1,2]. J. Med. Chem. 26:264-270.
Olson, F. et al. (1979) Preparation of liposomes of defined size distribution by extrusion through polycarbonate membranes. Biochimica et Biophysica Acta 557:9-23.

(Continued)

*Primary Examiner*—Jeffrey C Mullis
(74) *Attorney, Agent, or Firm*—DLA Piper LLP (US)

(57) ABSTRACT

Lipid prodrugs of pharmaceutical agents and their analogs that have increased anticancer, anti-viral, anti-inflammatory, anti-proliferative activity over the parent drug, and methods for making lipid prodrugs. Compositions comprising lipid prodrugs for treating disease and methods for treating disease which involve using the compositions.

35 Claims, 2 Drawing Sheets

OTHER PUBLICATIONS

Ruprecht, R. et al. (1986) Suppression of mouse viraemia and retroviral disease by 3'-azido-3'-deoxythymidine. Nature 323:467-469.

Seela, F. et al. (1987) Oligodeoxyribonucleotides containing 1,3-propanediol as nucleoside substitute. Nucleic Acids Research 15(7):3113-3129.

Stec. W. et al. (1976) Organophosphorus compounds of sulfur and selenium. Stereochemistry of oxidation of thiono- and selenophosphoryl compounds with hydrogen peroxide. J. Org. Chem. 41(2):233-238.

Szoka, F. et al. (1988) Increased efficacy of phosphonoformate and phosphonoacetate inhibition of herpes simplex virus type 2 replication by encapsulation in liposomes. Antimicrobial Agents and Chemotherapy 32(6):858-864.

Szoka, F. et al. (1978) Procedure for preparation of liposomes with large internal aqueous space and high capture by reverse-phase evaporation. Proc. Natl. Acad. Sci. 75(9):4194-4198.

Hostetler, K.Y. et al., Lipid prodrugs of phosphonoacids: greatly enhanced antiviral activity of 1-O-octadecyl-sn-glycero-3-phosphonoformate in HIV-1, HSV-1 and HCMV-infected cells, in vitro. Antiviral Research 31:59-67 (1996).

Calogeropoulou, T. et al. (1995) Synthesis and anti-HIV evaluation of alkyl and alkoxyethyl phosphodiester AZT derivatives. Antiviral Chem. & Chemother. 6(1): 43-49.

* cited by examiner

PRODRUGS OF PHARMACEUTICALS WITH IMPROVED BIOAVAILABILITY

GOVERNMENT LICENSE RIGHTS

This invention was made with government support under grant number GM24979 awarded by National Institutes of Health. The government has certain rights in the invention.

TECHNICAL FIELD

The present invention relates to lipid derivatives of pharmaceutical agents. It relates particularly to lipid prodrugs of pharmaceutical agents, methods for improving the oral and/or tissue bioavailability of pharmaceutical agents, and the use of inflammatory disease, and proliferative diseases.

BACKGROUND OF THE INVENTION

Drugs administered orally can be absorbed through the oral mucosa, through the lining of the stomach and primarily through the small and large intestines; however, the rate of absorption depends on the ability of the drug to pass through the lipid barrier of epithelial membranes. For example, alcohol, a lipid soluble, non-ionic compound, is rapidly absorbed into the blood stream by diffusion across the gastric mucosa. Weak acids are also well absorbed through the lining of the stomach, while weak bases are absorbed mainly in the small intestine. Drugs that are ionized, or lipid insoluble, for example, quaternary ammonium compounds and streptomycin, are poorly absorbed in the digestive tract, and must be administered by injection. Although injected drugs are not subject to the gastrointestinal barriers to bioavailability which are imposed on drugs administered orally, nonetheless, minimal tissue uptake or lack of tissue retention often interfere with the injected drug's bioavailability.

Under normal circumstances, intact dietary lipids, mostly triglycerides and phospholipids, are not readily absorbed through the intestinal mucosa. Phospholipids are present physiologically in the gut as phosphatidylcholine, phosphatidylethanolamine, phosphatidylinositol, phosphatidylserine, phosphatidylglycerol and phosphatidic acid. The normal physiological mechanism for lipid absorption requires conversion of the phospholipid to lysophospholipids by removal of the sn-2 acyl group by the hydrolytic action of the pancreatic enzyme phospholipase $A_2$ on the sn-2 acyl ester bond. Conversion of phospholipids to lysophospholipids provides the normal mechanism for absorption and transport of this class of lipids from the gut and accounts for the uptake of several grams of phospholipid per day.

While the need continues for less toxic, more selective, and more effective prodrugs of all types, bioavailability of pharmaceutical agents remains an important problem. Many oral drug candidates fail because of difficulty in oral absorption or in penetration of the cellular membranes of target tissues in the body after injection. Many intravenous, intraperitoneal, or other injectable drug candidates fail because of difficulty in penetrating cellular membranes of target tissues and/or failure to be retained in the tissue.

For example, the antiviral compounds phosphonoacetate and phosphonoformate, which were first synthesized in 1924 (Nylén, *Chem. Berichte* 57:1023), have the ability to inhibit viral enzymes selectively. This ability was not immediately demonstrated. Helgstrandi, et al., *Science* 201:819-821 (Sep. 1, 1978) disclosed that both phosphonoacetic acid and phosphonoformic acid inhibit several DNA polymerases and preferentially inhibit several viral DNA polymerases. Phosphonoformate and phosphonoacetate are presently known to selectively inhibit the DNA polymerase of many viruses, including human cytomegalovirus (HCMV), herpes simplex virus (HSV) and the reverse transcriptase of human immunodeficiency virus (HIV). Chrisp and Clissold ((1991) *Drugs* 41:104) review the pharmacology of these agents. Phosphonoacetate is too toxic for use in humans, but phosphonoformate (Foscavir, Astra) is approved for human use in HCMV-infected AIDS patients. However, it is not highly potent, requires prolonged intravenous administration and has substantial toxicity to the kidney and other organs. Ericksson, et al., U.S. Pat. Nos. 4,215,113; 4,339,445; 4,665,062; 4,771,041 teach the use of phosphonoformic acid as the selective agent in treating viral infections, including herpes virus type I and II and cytomegalovirus, in treating cancer caused by virus, and also opposing transformation of cells caused by oncogenic viruses.

Derivatized forms of phosphonoacids and pharmaceutical formulations comprising these compounds are known. U.S. Pat. No. 5,072,032 to McKenna discloses thiophosphonoacids; U.S. Pat. Nos. 4,386,081 and 4,591,583 to Helgstrand et al. disclose phosphonoformic acid esters of alkyl, alkylene, alkoxy and related cyclic and aromatic groups and some of these are shown to inhibit herpes virus and the functions and intracellular multiplications of influenza virus. U.S. Pat. No. 5,194,654 to Hostetler et al., discloses phospholipid derivatives of phosphonoacids, their incorporation into liposomes and their use as selective antiviral and antiretroviral agents.

It would be useful to identify chemical structures for pharmaceutical prodrugs which enhance oral bioavailability and/or cellular uptake and retention regardless of the route of administration. The optimized prodrugs would be metabolized in target tissues to release the pharmaceutical agent, which agent would persist in the target tissue to exert its intended action either directly or after metabolic conversion to the active form.

SUMMARY OF THE INVENTION

The present invention provides a series of improved prodrugs and their analogs having substantial increases in desired activity over the parent compounds against various cancers, viral diseases, autoimmune diseases, and other inflammatory and proliferative diseases.

In one aspect, the present invention provides compounds of the formula:

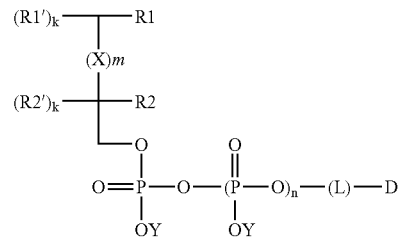

wherein R1 and R1' are each independently an O-alkyl or S-alkyl group, wherein the alkyl group comprises a linear or branched, substituted or unsubstituted $C_1$ to $C_{24}$ group, having from 1 to 6 double bonds; or an O-acyl or S-acyl moiety, wherein the acyl group comprises a linear or branched, substituted or unsubstituted $C_1$ to $C_{24}$ group, having from 1 to 6 double bonds;

X is CH—R2;

m=0 to 6;

each k is independently =0 or 1;

each R2 or R2' are independently selected from the group consisting of H, =O, the halogen group consisting of fluorine, chlorine, iodine and bromine; $O(CH_2)_p CH_3$ where p is 0 to 7; $NH_2$; O-alkyl or S-alkyl group, wherein the alkyl group comprises a linear or branched, substituted or unsubstituted $C_1$ to $C_8$ group having from 0 to 3 double bonds; O-acyl or S-acyl group, wherein the acyl group comprises a linear or branched, substituted or unsubstituted $C_1$ to $C_8$ group having from 0 to 3 double bonds; N-acyl group wherein the acyl group comprises a linear or branched, substituted or unsubstituted $C_1$ to $C_8$ group having from 0 to 3 double bonds; N-alkyl or N-dialkyl group wherein the alkyl group comprises a linear or branched, substituted or unsubstituted $C_1$ to $C_{24}$ group having from 0 to 6 double bonds;

wherein Y is $A^+$ when said compound is in the form of a salt or combination thereof, each $A^+$ is independently selected from the group consisting of $H^+$, $Na^+$, $Li^+$, $K^+$, $NH_4^+$; amines selected from the group consisting of mono-, di-, trialkylamines, and other physiologically acceptable cations;

n=0, 1, or 2;

wherein L is a linking molecule of the formula J—$(CH_2)_t$-G wherein J and G are functional groups independently selected from the group consisting of hydroxyl, sulfhydryl, carboxyl, and amine groups, wherein t=1 to 24; or L is absent; and wherein D is a drug having a functional group selected from the group consisting of hydroxyl, sulfhydryl, carboxyl and amino groups.

DETAILED DESCRIPTION OF THE PREFERRED EMBODIMENTS

Figure 1:
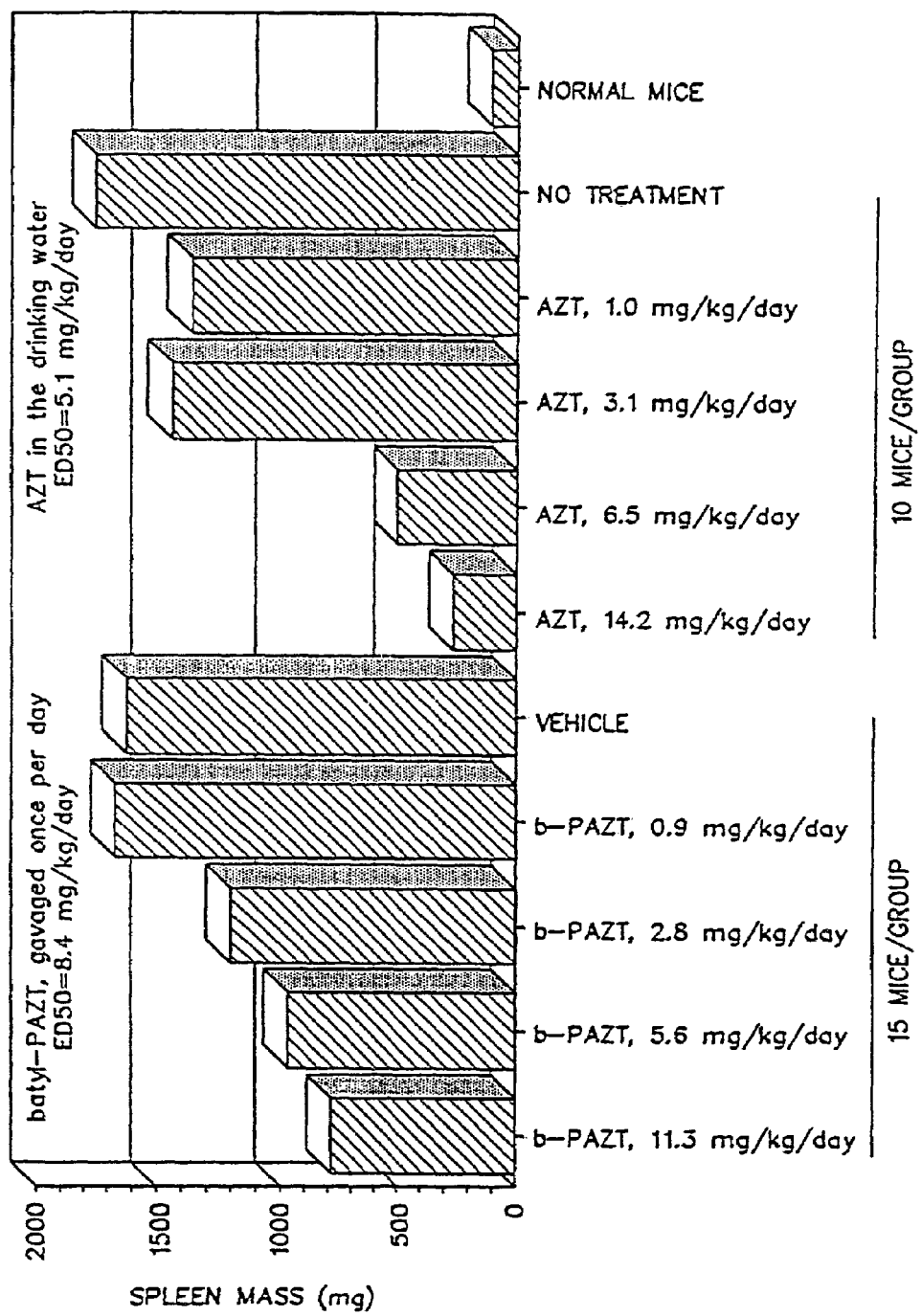
FIG. 1 shows spleen weights of mice treated with 1-O-octadecyl-sn-glycero-3-phospho-AZT.

It is an object of the invention to provide lipid prodrugs of pharmaceutical agents that retain the pharmacological effects of the parent compounds and which provide improved oral bioavailability and/or tissue bioavailability. Unexpectedly, it has been found that the compounds of the present invention have advantageous pharmacological effects either over previously known prodrugs of this type or over non-derivatized parent drugs. After oral, intravenous, intraperitoneal, intramuscular, subcutaneous or topical administration and upon uptake in the target tissues, the claimed prodrugs are converted to the active pharmaceuticals which persist intracellularly to exert their expected action. The claimed structures are advantageous in terms of target tissue uptake, conversion to active form, persistence in target tissue, and exertion of expected action. Accordingly, the compounds of the invention may be administered to subjects orally, intravenously, intraperitoneally, topically, subcutaneously, intramuscularly or by inhalation to treat diseases of mammals according to the use of the free, i.e. non-derivatized drug. In comparison to lipid-conjugate derivative prodrugs, the claimed lipid-conjugates of the same drugs demonstrate superior oral absorption and tissue uptake by virtue of the lack of a free hydroxyl group at the R2 position, as described below.

The invention accordingly provides a series of improved prodrugs and their analogs having substantial increases in desired activity over the parent compounds against various cancers, viral diseases, autoimmune diseases, and other inflammatory and proliferative diseases. These enhanced activities can be demonstrated in cell culture, for example, by means of the in vitro susceptibility assays described in Examples 35 to 37 and in pharmacokinetic experiments described in Example 38 and FIG. 2.

The invention provides compounds which are prodrugs of pharmaceutical agents and which have the advantage of improved bioavailability after oral, intravenous, intraperitoneal, intramuscular, subcutaneous or topical administration. A number of drugs that have poor bioavailability, whether by oral, intravenous, intraperitoneal, intramuscular, subcutaneous or topical route of administration, can be made suitable for a route of administration by conversion to the lipid derivatives of the invention, particularly to substituted or unsubstituted 1-O-alkyl-propanediol-phosphate derivatives, wherein an $C_8$ to $C_{24}$ alkyl group is attached to the 1-position of the propanediol moiety by an ether linkage. It has been determined that the improved oral bioavailability and/or tissue uptake of the compounds of the present invention relies on the lack of a free hydroxyl at the R2 position in the claimed compounds. The inventors do not fully understand the reasons for the improved bioavailability but hypothesize that without a free hydroxyl group at the R2 position, the claimed compounds cannot be metabolized to less favorable alkyl/acyl species in vivo, which species are less effective in oral absorption and in tissue uptake and retention in vivo. Furthermore, the propanediol lipid compounds lacking a hydroxyl at R2 are more hydrophobic and may cross cell membranes more effectively and may also be less cytotoxic.

The claimed method or strategy for making the claimed compounds is applicable to any drug which has a chemical group capable of covalently binding to a phosphate group or capable of covalently binding to a linking group that can covalently bind to a phosphate group. As disclosed herein, drugs or pharmaceutical agents having an available hydroxyl, sulfhydryl, carboxyl or amine group can be covalently linked by either strategy to a phosphate group of a 1-O-alkyl-propanediol-3-phosphate or to the corresponding 1-O-acyl, 1-S-alkyl, and 1-S-acyl analogs to promote improved bioavailability and/or tissue bioavailability of the drug. The linking group is a multifunctional molecule having the required covalent binding properties; for example, an hydroxylated carboxylic acid or an amino acid or a polypeptide.

The alkyl group of the alkylpropanediols of the invention can be a straight, branched or cyclic hydrocarbon chain, having from 2 to 24 carbons, and can be saturated or unsaturated with up to six double bonds. Preferably the alkyl group has 8 to 24 carbon atoms. Alkyl groups having from 16 to 20 carbon atoms are most preferred. Taking note of formula I below, particularly preferred are compounds wherein R1 is an O-octadecyl group. The alkyl group is attached to the propanediol moiety by an ether or vinyl ether bond. Also preferred are compounds wherein R2 is an O-benzyl or an $OCH_3$ group. In other embodiments, R1 may be attached to the sn-3 position of propanediol or glycerol while the phosphate, linker and drug moieties are attached at the sn-1 position. Alternatively, the lipid moieties may also be racemic.

According to yet another aspect of the invention, there are provided 2-carbon analogs of the compounds of the invention, the general structure of which is shown below.

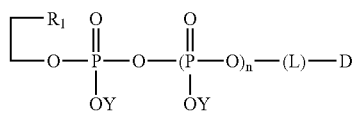

A preferred compound according to this embodiment is 1-O-octadecyl-1,2-ethanediol-2-phosphate adduct of pharmaceutical agents.

The preferred lipid derivatives of the invention are of the formula:

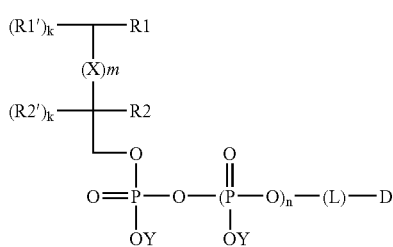

wherein R1 and R1' are each independently an O-alkyl or S-alkyl group, wherein the alkyl group comprises a linear or branched, substituted or unsubstituted $C_1$ to $C_{24}$ group, having from 1 to 6 double bonds; or an O-acyl or S-acyl moiety, wherein the acyl group comprises a linear or branched, substituted or unsubstituted $C_1$ to $C_{24}$ group, having from 1 to 6 double bonds;

X is CH—R2;

m=0 to 6;

each k is independently =0 or 1;

each R2 or R2' are independently selected from the group consisting of H, =O, the halogen group consisting of fluorine, chlorine, iodine and bromine; $O(CH_2)_pCH_3$ where p is 0 to 7;, $NH_2$; O-alkyl or S-alkyl group, wherein the alkyl group comprises a linear or branched, substituted or unsubstituted $C_1$ to $C_8$ group having from 0 to 3 double bonds; O-acyl or S-acyl group, wherein the acyl group comprises a linear or branched, substituted or unsubstituted $C_1$ to $C_8$ group having from 0 to 3 double bonds; N-acyl group wherein the acyl group comprises a linear or branched, substituted or unsubstituted $C_1$ to $C_8$ group having from 0 to 3 double bonds; N-alkyl or N-dialkyl group wherein the alkyl group comprises a linear or branched, substituted or unsubstituted $C_1$ to $C_{24}$ group having from 0 to 6 double bonds;

wherein Y is $A^+$ when said compound is in the form of a salt or combination thereof, each $A^+$ is independently selected from the group consisting of $H^+$, $Na^+$, $Li^+$, $K^+$, $NH_4^+$; amines selected from the group consisting of mono-, di-, trialkylamines, and other physiologically acceptable cations;

n=0, 1, or 2;

wherein L is a linking molecule of the formula $J—(CH_2)_t$-G wherein J and G are functional groups independently selected from the group consisting of hydroxyl, sulfhydryl, carboxyl, and amine groups, wherein t=1 to 24; or L is absent; and wherein D is a drug having a functional group selected from the group consisting of hydroxyl, sulfhydryl, carboxyl and amino groups.

Linking groups can be any of several molecules having multifunctional groups comprising hydroxyl, sulfhydryl, carboxyl, and amino groups. Particularly suitable for use as linkers are:

(1) the amino alcohols, having the general structure HO—$(CH_2)$—$NH_2$, where n=1 to 24, preferably where n=2 or 3, and suitable for insertion at the carboxyl group of a candidate drug which is an active drug moiety or a chemically modified drug. A 1-O-alkylpropanediol-3-phosphoethanolamine is a naturally occurring phospholipid that incorporates a linker of the amino alcohol type, and a 1-O-alkyl-propanediol-3-phosphoethanolamine can be conveniently coupled to drugs having an available carboxyl group to prepare a lipid prodrug of the invention.

(2) the hydroxyalkyl carboxylic acids, having the general structure HO—$(CH_2)_n$—COOH, where n=1 to 12, and suitable for insertion at the amino group of an active candidate drug. Naturally occurring molecules such as hydroxy fatty acids, beta-hydroxybutyric acid, and hydroxyamino acids such as serine and hydroxyproline may also be conveniently used.

Finally, the phosphate-linker-drug moiety of the invention may be replaced by phosphonoformate, phosphonoacetate, thiophosphonoformate and thiophosphonoacetate or their respective carboxymethyl or carboxyethyl esters.

The present invention provides claimed structures of pharmaceutical agents and methods of use which provide advantages compared to the free, non-derivatized forms of the pharmaceutical agents in terms of target tissue uptake, conversion to active form, persistence in target tissue, and exertion of expected action. Advantages of the claimed structures and methods are manifest as improved usefulness, efficacy, biological half life, transport across cellular membrane, i.e. bioavailability after oral, intravenous, intraperitoneal, intramuscular, subcutaneous or topical administration of any drug having a chemical structure suitable for binding as described herein. The method of the invention is advantageously applicable to drugs that are poorly bioavailable, regardless of route of administration. Examples of the variety of therapeutic classes of drugs that can be effectively administered by the oral route comprise 1-O-alkyl, 1-O-acyl, 1-S-alkyl (thioether), or 1-S-acyl (thioester) propanediol derivatives of:

(a) anticancer agents, comprising nucleoside, analogs, for example, 1-β-D-arabinofuranosylcytosine (hereinafter, cytosine arabinoside or ara-), 9-β-D-arabinofuranosyladenine (hereinafter, adenine arabinoside or ara-A), 5-fluorouridine, 6-mercaptopurine riboside, or 2'-arafluoro-2-chlorodeoxyadenosine;

(b) antiviral nucleosides, particularly the 1-O-alkyl-propanediol-3-phosphate derivatives of acyclovir, ganciclovir and the antiviral nucleosides disclosed in U.S. Pat. No. 5,223,263, which is hereby incorporated by reference;

(c) therapeutic peptides or peptidomimetics, or peptides that are enzyme inhibitors, comprising D-amino acids, L-amino acids, or amino-acid analogs, and having up to about 35 amino acids, preferably less than 6 amino acids, or analogs thereof, particularly the lipid derivatives disclosed in U.S. Pat. No. 5,554,728, which is hereby incorporated by reference. In a preferred embodiment of this species, a 1-O-alkyl-propanediol-3-phosphate derivative of desmopressin, n-muramyl tripeptide, or enalkiren is synthesized and administered orally.

(d) antibiotics, particularly those of the penicillin and cephalosporin class, including penicillin G, cefazolin, ceftazidime, ceftriaxone, or piperacillin.

(e) phosphonoacid compounds, particularly the 1-O-alkyl propanediol derivatives of phosphonoformic acid and phosphonoacetic acid, and nucleoside phosphonates disclosed in U.S. Pat. No. 5,194,654;

(f) 5-amino(1-beta-D-ribofuranosyl) imidazole carboxamide or 1-beta-D-ribofuranosyl 1,2,4-triazole-3-carboxamide, which are used for the treatment of allergy, including asthma and urticaria eczema; autoimmune disease, including Lesch-Nyhan disease, cardiac disorders related to restricted blood flow or viral diseases.

(g) non-steroidal anti-inflammatory compounds, particularly the 1-O-alkylphospholipid derivatives of these compounds disclosed in U.S. Pat. No. 5,744,592.

Table 1 lists preferred drug candidates for the method of the invention according to therapeutic class.

TABLE 1

Candidate Drugs for Preparation of Orally Bioavailable Lipid Prodrugs

| THERAPEUTIC CLASS | | MERCK INDEX |
|---|---|---|
| I. | Antineoplastic agents | |
| | actinomycin D | |
| | bleomycin | 1324 |
| | cisplatin and Pt analogs: | |
| | carboplatin, iproplatin | 2319, 1828 |
| | cytosine arabinoside | 2790 |
| | daunorubicin | 2825 |
| | doxofluoridine | 3426 |
| | doxorubicin | 3428 |
| | etoposide | 3842 |
| | floxuridne | 4045 |
| | mithramycin | |
| | mitomycin C | 6133 |
| | mitoxanthrone | 6135 |
| | pentostatin (deoxycoformycin) | 7091 |
| | phosphonoacids | |
| | streptozotocin | 8794 |
| | taxol and taxotere | 9049 |
| | vinca alkaloids: | |
| | vincristine | 9291 |
| | vinblastine | 9887 |
| | vindesine | 9892 |
| II. | Anti-Infectives aminoglycerides: | |
| | netilmycin | 6389 |
| | amikacin | 416 |
| | gentamycin | 4284 |
| | streptomycin | 8786 |
| | kanamycin A | 5161 |
| | tobramycin | 9413 |
| | neomycin B | 6369 |
| | pliocarmycin | 7510 |
| | amphotericin B | 620 |
| | vancomycin | 9869 |
| III. | Antivirals | |
| | 3'-azido-3'-deoxythymidifle (AZT; anti-HIV) | 139 |
| | acyclovir (herpes simplex, anti-HSV) | 4166 |
| | foscarnet | 4166 |
| | ganciclovir (anti-CMV) | 4262 |
| | idoxuridine (anti-HSV keratitis) | 4262 |
| | ribavirin | 8199 |
| | 5-fluoro-3'-thia-2', 3'-dideoxcytidine (anti-HBV, HIV) | 9599 |
| | trifluridine (herpes group, eye) | |
| | vidarabine (HSV encephalitis) | 9881 |
| IV. | Short Peptides or peptidomimetics | |
| | corticotropin (ACTH) | 127 |
| | calcitonin | 1640 |
| | desmopressin (DDAVP) | 2904 |
| | gonadotropin RH (LH-RH) | 5354 |

TABLE 1-continued

Candidate Drugs for Preparation of Orally Bioavailable Lipid Prodrugs

| THERAPEUTIC CLASS | | MERCK INDEX |
|---|---|---|
| | goserelin (LHRF) | 4433 |
| | insulin | 4887 |
| | lypressin | 5503 |
| | beta-melanotropin (β-MSH) | 6206 |
| | alpha-melanotropin (α-MSH) | 6206 |
| | muramyl dipeptide | 6214 |
| | oxytocin | 6934 |
| | vasopressin | 9843 |
| | FK-506 | |
| | octreotide | 6682 |
| | enalkiren renin inhibitor | |
| | aspartyl protease inhibitors (anti-HIV) | |
| | serine protease inhibitors | |
| V. | Miscellaneous Agents | |
| | morphine (narcotic analgesic) | 6186 |
| | prostaglandins | 7891 |
| | leukotrienes | 5339 |
| | cyclosporins (immunosuppressive) | 2759 |

A significant aspect of the compounds of the invention and related methods for oral administration of drugs is that 1-O-alkyl-, 1-O-acyl-, 1-S-alkyl-, and 1-S-acylpropanediol-3-phosphate derivatives require no metabolic conversions for oral absorption. These lipid prodrugs are in this way distinct from phosphatidyl derivatives, for which metabolic processing requires preliminary conversion to a lysophospholipid. Furthermore, the alkyl group at the 1-position of the propanediol moiety of the 1-O-alkyl derivative cannot be degraded by intestinal lysophospholipases because of the ether bond linking the alkyl group to the glycerol structure. This metabolic feature prevents digestive degradation and facilitates the intestinal uptake of the intact 1-S-alkyl- and 1-O-alkyl-propanediol-3-phosphate drug conjugate together with other lysophospholipids that are undergoing membrane transport in the small intestine. The 1-O-acyl and the corresponding thioester analogs may also be absorbed substantially but are less preferred in applications wherein this property is required.

In contrast to the prior 1-O-alkyl-glycero-phospho-drug compounds, an important design feature of the lipids of this invention is the absence of a free hydroxyl at the 2-position of glycerol. This prevents the formation of unfavorable 1-alkyl, 2-acyl-glycero-phosphate-drug metabolites which may not be subject to prompt passage through the small intestine and, further, may not be metabolized readily intracellularly to yield the desired active drug moiety. In addition, the compounds of the invention are more hydrophobic and may cross cell membranes more readily and may exhibit less cytotoxicity.

Coupling of Lipid Moiety to a Candidate Drug

The compounds of the invention are formed according to synthetic procedures which couple a substituted or unsubstituted 1-O-alkyl-propanediol-3-phosphate, or 1-O-acyl, 1-S-alkyl, or 1-S-acyl analogs thereof to a drug or which couple a substituted or unsubstituted 1-O-alkyl propanediol or 1-O-acyl, 1-S-alkyl, or 1-O-acyl analogs thereof, to a phosphorylated functional group of a drug.

The 1-O-alkyl propanediol moiety, or any other analog described above, and the drug can be covalently linked through mono-, di-, or triphosphate groups at the 3 position of the propanediol structure. When the 1-O-alkyl propanediol and the drug are joined through a linking group, the linker molecule is conveniently attached to the terminal phosphate of, for example, 1-O-alkyl-propanediol-3-phosphate. In either case, the candidate drug has an available functional group.

A reaction is typically carried out at a temperature of 25° to 60° C., preferably 30° to 50*C for a period of from 2 to 25 h, preferably 8 to 10 h. N,N'-Dicyclohexylcarbodiimide (DCC) is added in measured portions generally over a period of 0.5 to 3 h, preferably 0.75 to 1.5 h.

The reaction mixture is worked up by addition of water and azeotroped by successive additions of toluene and ethanol. The resulting crude product is purified by ion exchange and silica chromatography to afford the desired compound with the desired purity.

The process of the invention is preferably conducted in the liquid phase. Upon addition of either triisopropylbenzenesulfonyl chloride (TIPS) or N,N'-dicyclohexylcarbodiimide (DCC), the reaction mixture is heated to a temperature of 30° to 60° C. It is noted that the presence of equivalent (or more than stoichiometric), amounts of either TIPS or DCC does not impede the course of the reaction.

The temperature of the reaction mixture can rise up to its boiling point. The heat of the reaction can be removed by external cooling of the reaction vessel or by means of a cooled reflux condenser.

Suitable solvents for the reaction are amines or derivatives thereof. Preferred solvents include tertiary amines such as diisopropylethylamine, triethylamine, tributylamine, or heterocyclic amines such as pyridine or picolines.

1-O-alkyl analogs of the invention, for example, 1-O-octadecyl-propanediol-3-phosphate derivatives, or any of the other 1-O-acyl or 1-S-acyl or 1-S-alkyl analogs, can be produced by any of the synthetic organic procedures known to those in the art, for example, condensation of 1-O-alkyl-propanediol and the monophosphate of the drug candidate such as ara-C monophosphate as described in Example 2 (compound IIa). An alternative approach links 1-O-alkylpropanediol-3-phosphate to the hydroxyl of a candidate drug in the presence of a condensing agent such as DCC or TIPS (Example 5).

In another variation of the method, 1-O-octadecyl-2-benzyl-sn-glycero-3-phosphate was condensed with ara-C while the hydroxy group in 2-position of the batyl alcohol was protected as the benzyl ether.

Lipid Prodrug Derivatives of Taxol-Related Compounds

Lipid derivatives of taxol are prepared according to a procedure wherein the amino alcohol and hydroxy carboxylic acid units of the taxol side chain are covalently attached to a phosphatidic acid, preferably a 1-O-alkyl propanediol-3 phosphate as set forth in Examples 13 through 16. The side chain can be derivatized by the insertion of an aliphatic group $(CH_2)_n$ to increase lipophilicity.

According to the general procedure, a substituted β-amino-α-hydroxy-benzene propanoate is covalently linked to a phosphatidylglycerol or a 1-O-alkyl- or 1-O-acyl-2 benzyl-sn-glycero-3-phosphatidic acid in the presence of a condensing agent, such as DCC, to provide compounds of the formula:

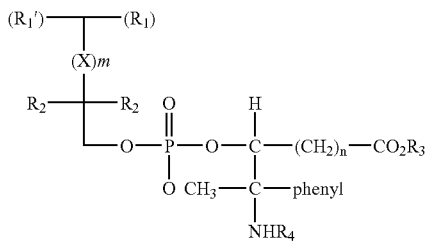

wherein
$R_3$ is any hydrolyzable ester group, for example, methyl, ethyl, or pivaloyl;
$R_4$ is benzoyl, pivaloyl, acetate, peptides, or amino acids; and
n is 0-10.

In alternative embodiments, $R_1$ and $R_2$ are attached to the glycerol group by thioester or thioether bonds.

In a preferred embodiment, $R_1$ is an ether-linked 1-0-octadecyl propanediol group, and $R_4$ is benzyl, and an 1-O-alkyl-propanediol-3-phosphate is condensed with a β-(benzoylamino)-α-hydrobenzene propanoate ester to form a lipid derivative of the taxol side chain. The propanoate ester is then hydrolyzed to yield the propanoic acid which is ready for coupling with baccatin III, or 10-deacetyl baccatin, having the formula:

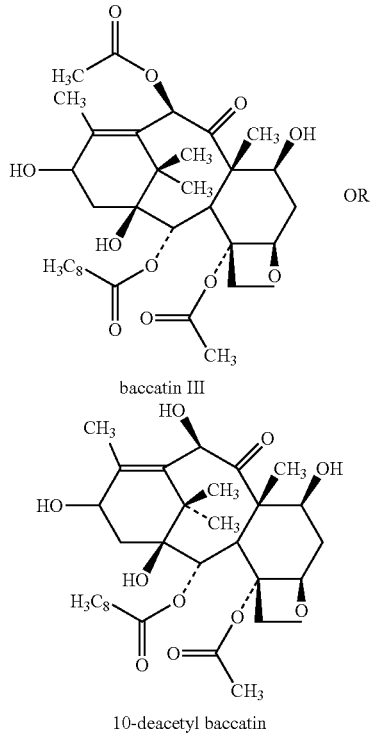

to form an orally bioavailable taxol compound.

Lipids comprising fatty acids, fatty alcohols, glycerides, and phospholipids for use in preparing the lipid prodrugs of the invention may be purchased from commercial suppliers (Avanti Polar Lipids, Inc., Pelham, Ala.; or Genzyme Corp., Cambridge, Mass.) or may be synthesized according to known methods. 1-O-octadecyl-sn-glycerol (batyl alcohol) is available from Sigma, St. Louis, Mo., and a 2-benzyl derivative of batyl alcohol is available from Bachem, Inc., Basel, Switzerland. Other lysophosphatidic acids useful in preparing the prodrugs of the invention are available from Genzyme, Cambridge, Mass. The drugs to which these lipids are covalently linked can be purchased from the pharmaceutical manufacturers.

It is important that all traces of water be removed from the reactants in order for the coupling reactions to proceed. Therefore, the lipids are first either freeze-dried by solvent evaporation under vacuum, or in a vacuum oven over $P_2O_5$. The reactions are also carried out under an inert gas, such as, for example, argon.

The synthetic reactions are followed using thin layer chromatography (TLC) with appropriate solvents. When the reaction is complete as determined by TLC, the product is extracted with an organic solvent and purified by chromatography on a support suitable for lipid separation, for example, silicic acid.

Efficacy and Potency of 1-O-alkyl-Propanediol-3-Phosphate Prodrugs

The lipid derivative prodrugs of the invention, preferably 1-O-alkyl-propanediol-3-phosphate prodrugs, have advantageous pharmacological properties in comparison to the non-derivatized drugs.

The efficacy of the lipid prodrugs of the invention was demonstrated in tests carried out both in vitro and in vivo. 1-O-Octadecyl-sn-glycero-3-phospho-3'-azido-3'-deoxythymidine (AZT) was used in oral absorption studies. This compound has an 18-carbon alkyl ether at position 1 of glycerol; the hydroxyl at position 2 of glycerol is open, and position 3 is linked by a phosphodiester bond to 3'-azido-3'-deoxythymidine (AZT)-5'-monophosphate. 1-O-octadecyl-sn-glycero-3-phospho-AZT does not require any metabolic conversions for absorption and appears to be absorbed directly from the gastrointestinal tract. It is not subject to deacylation by lysophospholipases in the gut because of the ether bond at position 1 of glycerol. Its metabolism is not known but it is hypothesized that the compound is metabolized by cellular enzymes and phosphodiesterases releasing 3'-azido-3'-deoxythymidine (AZT) or AZT-MP inside the cell.

The in vivo study as described in Example 16 demonstrates that a 1-O-alkyl-sn-glycero-3-phosphate drug derivative has the same pharmacological efficacy as that of the non-derivatized agent. It further demonstrates that oral dosing with the 1-O-octadecyl-glycero-3-P derivative can allow more convenient and effective administration of AZT. 1-O-Octadecyl-sn-glycero-3-phospho-AZT was compared to free AZT in treating mice infected with Rauscher murine leukemia virus (RLV). RLV is a murine retrovirus, and RLV-infected mice are useful as a model system for evaluating therapeutic effectiveness of candidate anti-AIDS drugs against retrovirus induced disease in vivo. RLV infects splenocytes and the infected animals exhibit massive splenomegaly. Effective antiviral agents inhibit the splenomegaly, and a reduction in organ weight correlates with the elimination of virus (Ruprecht, R., et al., *Nature* 323:467-469 (1986)). Because AZT has a short physiological half-life, the most effective mode of AZT therapy should be continuous oral administration. The closest practical approach to optimum administration is the intake of AZT in drinking water. Oral administration of batyl-P-AZT on a once a day regimen of gavage proved to be as effective, in comparable doses, as virtually continuous free AZT administration, as determined by inhibition of splenomegaly in the infected mice (FIG. 1).

It is anticipated that the lipid compositions of the invention, when linked to AZT, will have equivalent or superior activity to 1-O-octadecyl-sn-glycero-3-P-AZT.

Lipid Prodrugs of the Phosphonoacids

It is an object of the invention to provide lipid prodrugs of the phosphonoacids that retain the pharmacological effects of the parent compounds. Unexpectedly, it has been found that the compounds of the present invention have advantageous pharmacological effects over previously known prodrugs of this type. The invention accordingly provides a series of improved prodrugs of phosphonoformate and phosphonoacetate and their analogs having substantial increases in antiviral activity over the parent compounds against human cytomegalovirus (HCMV), herpes simplex virus (HSV), and human immunodeficiency virus (HIV-1) This enhanced antiviral activity can be demonstrated in cell culture, for example, by means of the in vitro susceptibility assays described in Examples 35-37.

Synthesis of Improved Prodrugs of the Phosphonoacids

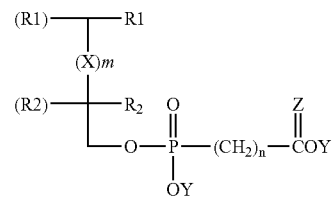

The compounds that are synthesized are outlined in Scheme I with the various substitutes on C1, C2 and C3 of the glycerol, and similarly in Schemes II and III for compounds wherein $(X)_m$ is $(CH—R2)_m$ and $m>1$.

Identification of Starting Materials and Products

The phosphonoacids to which various lipid moieties are coupled in the preparation of the lipid prodrugs of the invention are designated by acronyms, as follows:

n=0, Z=O (PFA) Phosphonoformic acid n=0, Z=S (PFSA) Thiophosphonoformic acid n=0, Z=Se (PFSeA) Selenophosphonoformic acid n=1, Z=O (PAA) Phosphonoacetic acid n=1, Z=S (PASA) Thiophosphonoacetic acid n=1, Z=Se (PASeA) Selenophosphonoacetic acid The various lipid prodrug derivatives are designated herein by acronyms derived from those above, and defined in the legends of Tables I-III.

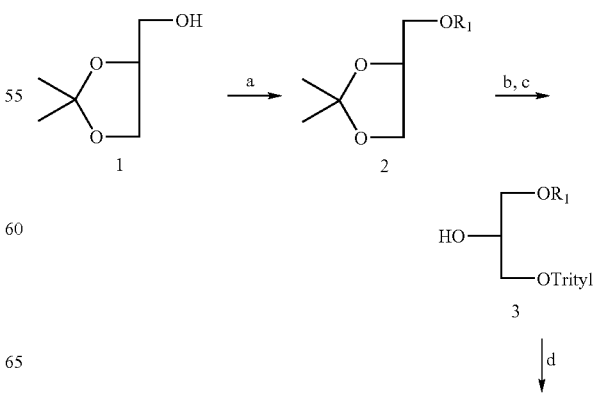

-continued

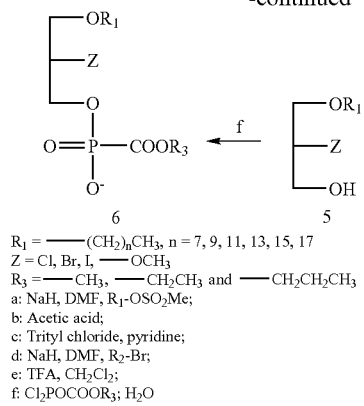

R₁ = —(CH₂)ₙCH₃, n = 7, 9, 11, 13, 15, 17
Z = Cl, Br, I, —OCH₃
R₃ = —CH₃, —CH₂CH₃ and —CH₂CH₂CH₃
a: NaH, DMF, R₁-OSO₂Me;
b: Acetic acid;
c: Trityl chloride, pyridine;
d: NaH, DMF, R₂-Br;
e: TFA, CH₂Cl₂;
f: Cl₂POCOOR₃; H₂O SCHEME II
Example: Synthesis of phoshonoformic acid analog
x = CHOH, m = 1, R2 = OH, R1 = Octadecyl

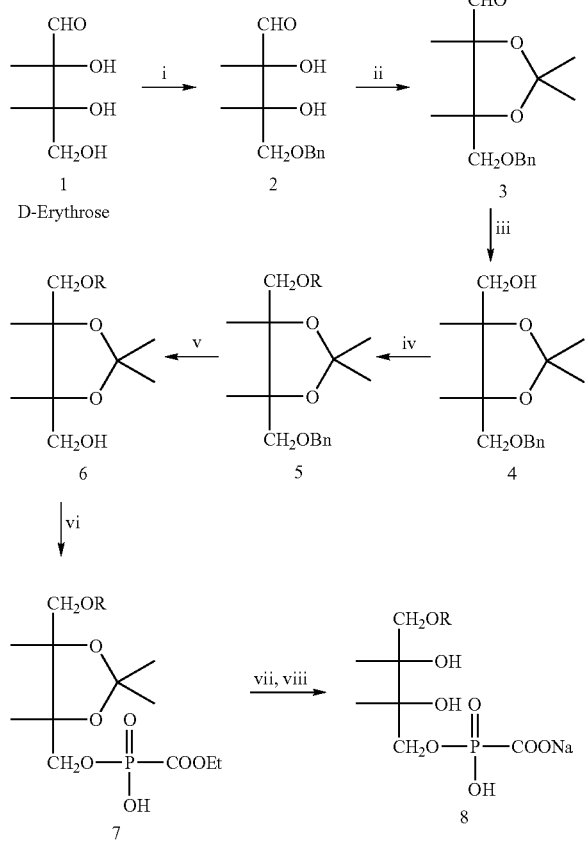

i. BuBr;
ii. DMP, H⁺;
iii. NaBH₄;
iv. ROSO₂Me (R = Octadecyl), NaH;
v. H₂, Pd/C;
vi. DCC, ethyl phoSphonoformate;
vii. TFA, CH₂Cl₂;

SCHEME III
Example: Synthesis of phosphonoformic acid analog
X = CHOH, m = 2, R2 = OH, R1 = Octadecyl

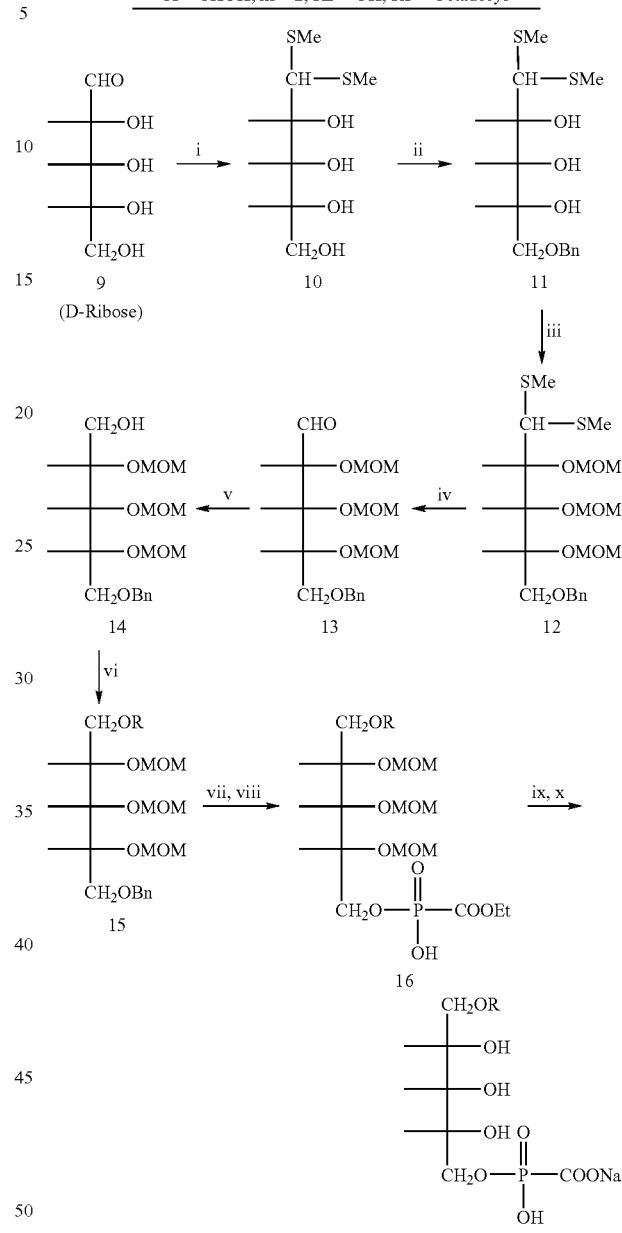

i. MeSSiMe₃, ZnI₂;
ii. BnBr, NaH;
iii. CH₃OCH₂Cl (MOM chloride), NaH, THF;
iv. AgNO₃, Ag₂O;
v. NaBH₄;
vi. ROSO₂Me, NaH;
vii. H₂, Pd/C;
viii. DCC, ethyl phosphonoformate;
ix. Acetic acid;
x. NaOH, ethanol Synthesis Procedures Lipid prodrugs of the phosphonoacids listed above are prepared according to the procedures described in Examples 28, 29 and 33. A synthesis flow diagram particularly relevant to the synthesis of compounds wherein m=0 and Y is absent is set forth in Scheme I; flow diagrams particularly relevant to the chemical synthesis of compounds wherein m>0 and Y is present are set forth in Schemes II and III.

Antiviral Activity

The antiviral activity of various lipid derivatives of phosphonoacids according to the invention was determined in cultures of human cell lines infected with HCMV, HSV, or HIV-1 as described in Examples 35-37. The results are shown in Tables I-III. The predictive value of in vitro susceptibility testing for virus infections is discussed by Kern, E. R. (1990) Preclinical evaluation of antiviral agents: In vitro and animal model testing. Galasso, G. et al. eds., *Antiviral Agents and Viral Disease of Man*, 3rd Edition, Raven Press, NY, pp. 87-123.

The most preferred compounds which exhibit greatly increased antiviral activity (Tables I-III) have 1-O-alkyl groups at R1, and O-methyl or O-benzyl or 2,2-dimethoxy at R2.

Antiviral activity of the improved phosphonoacid prodrugs against human cytomegalovirus-infected MRC5 human lung fibroblast cells is shown in Table I. The most preferred prodrugs of phosphonoformate have remarkable increases in antiviral activity. Previous attempts to produce prodrugs of phosphonoformate with increased activity have identified a few compounds which have very small increases in activity, but no compound having increases in activity over PFA greater than 1.9 fold have been shown previously (Norén, J. O., et al., *J. Med. Chem.* 26:264-270, 1983). The most active PFA prodrugs, B-PFA, BB-PFA, MB-PFA, and ODDMOP-PFA exhibit 107-, 72-, 38- and 209-fold increases in activity and represent the most active PFA-containing compounds yet reported. These compounds have a 1-O-alkyl group at the R1 position of glycerol and either a hydroxyl, —O-benzyl or —O-methyl or 2,2 dimethoxy function at the R2 of glycerol or propane. Prodrugs having H, halogen or amino at R2 will also be highly active and substitution at X of S or Se for O will provide similar results.

The improved PFA prodrugs also exhibit greatly increased activity versus PFA in herpes simplex virus-1 infected human lung fibroblasts (Table II). MB-PFA, B-PFA and BB-PFA are 72-, 43- and 34-times more active than PFA and represent the most active PFA derivatives yet reported. The order of activity is slightly different from that observed with human cytomegalovirus; MB-PFA is the most active compound followed by B-PFA and BB-PFA. Similar results were obtained with human immunodeficiency virus-1 infected cells in vitro (Table III). With HIV-1, MB-PFA was the most active compound followed by B-PFA and BB-PFA; the compounds were 104-, 37- and 9-fold more active than PFA in HIV-infected HT4-6C cells and represent the most active anti-HIV derivatives of PFA reported. MB-PFA was more active than B-PFA to a statistically significant degree (Table III).

Therapy of Viral Diseases

The lipid derivatives of antiviral nucleoside analogs and phosphonoacids disclosed herein are useful in treating diseases caused by viruses such as influenza, herpes simplex virus (HSV), human herpes virus 6, cytomegalovirus (CMV), hepatitis B virus, Epstein-Barr virus EBV), and varicella zoster virus (VZV). They are useful in the treatment of AIDS and other retroviral diseases, as well.

Lipid derivatives of antiviral drugs may be applied topically to the skin, eyes or mucus membranes or into the interior of the body, for treating susceptible virus infections in man and animals. They can be introduced internally, for example orally, intratracheally or otherwise by the pulmonary route, enternally, rectally, nasally, vaginally, lingually, intravenously, intra-arterially, intramuscularly, intraperitoneally, intradermally, or subcutaneously. The present pharmaceutical preparations can contain the active agent alone, or can contain further pharmaceutically valuable substances. For example, formulations comprising lipid phosphonoacid prodrugs of the invention can additionally comprise another antiviral agent, such as for example, a viral protease inhibitor, or an antiviral nucleoside analog. They can further comprise a pharmaceutically acceptable carrier.

Lipid derivatives of antiviral agents may have a prolonged antiviral effect as compared to the lipid-free agents; therefore they provide therapeutic advantages as medicaments even when not incorporated into liposomes.

These phosphonoacid prodrug antiviral agents may be used alone or in combination with antiviral nucleosides as given conventionally. The use of combination therapy may greatly reduce the tendency for drug resistant HIV mutant strains to appear and would therefore increase the likelihood of stopping the progression of HIV infection. The same argument would hold equally well in treating cytomegalovirus or herpes virus infections with regard to the likelihood of developing resistant strains.

Formulations

Pharmaceutical preparations containing lipid derivatives of antiviral nucleoside analogs or phosphonoacids are produced by conventional dissolving and lyophilizing processes to contain from approximately 0.1% to 100%, preferably from approximately 1% to 90% of the active ingredient. They can be prepared as ointments, salves, tablets, capsules, powders or sprays, together with effective excipients, vehicles, diluents, fragrances or flavor to make the formulations palatable or pleasing to use.

Formulations for oral ingestion are in the form of tablets, capsules, pills, ampules of powdered active agent, or oily or aqueous suspensions or solutions. Tablets or other non-liquid oral compositions may contain acceptable excipients, known to the art for the manufacture of pharmaceutical compositions, comprising diluents, such as lactose or calcium carbonate; binding agents such as gelatin or starch; and one or more agents selected from the group consisting of sweetening agents, flavoring agents, coloring or preserving agents to provide a palatable preparation. Moreover, such oral preparations may be coated by known techniques to further delay disintegration and absorption in the intestinal tract. The preparations can also comprise bile salts and detergents.

Aqueous suspensions may contain the active ingredient in admixture with pharmacologically acceptable excipients, comprising suspending agents, such as methyl cellulose; and wetting agents, such as lecithin, lysolethicin or long-chain fatty alcohols. The said aqueous suspensions may also contain preservatives, coloring agents, flavoring agents and sweetening agents in accordance with industry standards.

Preparations for topical and local application comprise aerosol sprays, lotions, gels and ointments in pharmaceutically appropriate vehicles which may comprise lower aliphatic alcohols, polyglycols such as glycerol, polyethylene glycol, esters of fatty acids, oils and fats, and silicones. The preparations may further comprise antioxidants, such as ascorbic acid or tocopherol, and preservatives, such as p-hydroxybenzoic acid esters.

Parenteral preparations comprise particularly sterile or sterilized products. Injectable compositions may be provided containing the active compound and any of the well known injectable carriers. These may contain salts for regulating the osmotic pressure.

Liposomal Formulations

If desired, the claimed compounds can be incorporated into liposomes by any of the reported methods of preparing liposomes for use in treating viral diseases such as, but not limited to HCMV, HSV, and HIV-1. The present invention may utilize the antiviral derivatives noted above incorporated in liposomes in order to direct these compounds to macrophages, monocytes, other cells and tissues and organs which take up the liposomal composition. The liposome-incorporated antiviral derivatives of the invention can be used to treat HCMV, HSV or AIDS patients by parenteral administration, enhancing delivery of the antiviral compound to macrophages and monocytes, an important reservoir of viral infections. This will allow for the efficacious use of lower doses of the modified phosphonoacids, reducing toxicity of the compound. Ligands may also be incorporated to further focus the specificity of the liposomes.

The derivatives described have several unique and novel advantages over the liposomal water soluble antiviral drugs. First, they can be formulated in liposomes to much higher ratios of drug to lipid because they are incorporated into the wall of the liposome instead of being located in the aqueous core compartment. Secondly, the liposomes containing the lipophilic antiviral derivatives noted above do not leak during storage, providing improved product stability. Furthermore, these compositions may be lyophilized, stored dry at room temperature, and reconstituted for use, providing improved shelf life. They also permit efficient incorporation of antiviral compounds into liposomal formulations without significant waste of active compound. A further advantage is that the compositions used in in vivo treatment cause a larger percentage of the administered antiviral prodrug to reach the intended target. For example, the use of the compositions reduces the amount being taken up by the kidney and bone, thereby decreasing the toxic side effects of the phosphonoacid drugs. The toxic side effects of the phosphonoformates may be further reduced by targeting the liposomes in which they are contained to actual or potential sites of infection by incorporating ligands into the liposomes. The liposome-incorporated lipid-antiviral conjugate is administered to patients by any of the known procedures utilized for administering liposomes. The liposomes can be administered intravenously, intraperitoneally, intramuscularly, intravitreally or subcutaneously as a buffered aqueous solution. Any pharmaceutically acceptable aqueous buffer or other vehicle may be utilized so long as it does not destroy the liposome structure or the activity of the lipid phosphonoacid analog. One suitable aqueous buffer is isotonic sorbitol containing 5 mM sodium phosphate with a pH of about 7.4, or other physiological buffered salt solutions.

The therapeutically effective amount of the lipid derivatives is determined by reference to the recommended dosages of the active antiviral drug, bearing in mind that, in selecting the appropriate dosage in any specific case, consideration must be given to the patient's weight, general health, metabolism, age and other factors which influence response to the drug. The dosage for a mammal, including a human, may vary depending upon the extent and severity of the infection and the activity of the administered compound. Dosage levels of liposomal lipid analogs of antivirals will be about the same as for the antiviral itself. Dosage levels for antiviral nucleosides and phosphonoformate through conventional administration by intravenous infusion are well established (Lambert, R., et al. (1989) *J. Med. Chem.* 32:367-374; Szoka, F. and Chu, C-J., *Antimicrobial Agents and Chemotherapy* 32(6):858-864 (1988); Ericksson et al. U.S. Pat. No. 4,771,041). Foscarnet is administered by i.v. infusion at 200 mg/kg/day for treatment of HCMV in humans.

The phosphonoacid prodrugs of the invention are administered to the patient on a daily basis in an oral dose of about 0.1 mg/kilogram to 1000 mg/kilogram and more preferably from about 1 mg/kilogram to about 200 mg/kilogram. The parenteral dosage will be appropriately 20 to 100% of the oral dose.

Liposome Preparation

After synthesis and purification, the lipid derivative of the antiviral is incorporated into liposomes, or other suitable carrier. The incorporation can be carried out according to well known liposome preparation procedures, such as sonication and extrusion. Suitable conventional methods of liposome preparation include, but are not limited to, those disclosed by Bangham, et al. (Bangham, A. D., Standish, M. M. and Watkins, J. C. (1965) *J. Mol. Biol.* 23:238-252.) Olson, et al. (Olson, F., Hunt, C. A., Szoka, F. C., Vail, W. J. and Papahadjopoulos, D. (1979) *Biochim. Biophys. Acta* 557:9-23), Szoka, F. and Papahadjopoulos, D. (1978) *Proc. Nat. Acad. Sci.* 75:4194-4198, Mayhew, E. et al. (1984) *Biochim. Biophys. Acta* 775:169175), Kim, S. et al. (1983) *Biochim. Biophys. Acta* 728:339:348, and Mayer, et al. (1986) *Biochim. Biophys. Acta* 858:161-168.

The liposomes may be made from the lipid derivatives of antivirals in combination with any of the conventional synthetic or natural phospholipid liposome materials including phospholipids from natural sources such as egg, plant or animal sources such as phosphatidylcholine, phosphatidylethanolamine, phosphatidylglycerol, sphingomyelin, phosphatidylserine, or phosphatidylinositol. Synthetic phospholipids that may also be used, include, but are not limited to: dimyristoylphosphatidylcholine, dioleoylphosphatidylcholine, dipalmitoylphosphatidylcholine and distearoylphosphatidycholine, and the corresponding synthetic phosphatidylethanolamines and phosphatidylglycerols. Cholesterol or other sterols, cholesterol hemisuccinate, glycolipids, cerebrosides, fatty acids, gangliosides, sphingolipids, 1,2-bis(oleoyloxy)-3-(trimethyl ammonio) propane (DOTAP), N-[1-(2, 3-dioleoyl) propyl-N,N,N-trimethylammonium chloride (DOTMA), and other cationic lipids may be incorporated into the liposomes, as is known to those skilled in the art. The relative amounts of phospholipid and additives used in the liposomes may be varied if desired. The preferred ranges are from about 60 to 90 mole percent of the phospholipid; cholesterol, cholesterol hemisuccinate, fatty acids or cationic lipids may be used in amounts ranging from 0 to 50 mole percent. The amounts of antivirals incorporated into the lipid layer of liposomes can be varied with the concentration of their lipids ranging from about 0.01 to about 50 mole percent.

Using conventional methods, approximately 20 to 30% of the free phosphonoacid present in solution can be entrapped in liposomes; thus, approximately 70 to 80% of the active compound is wasted. In contrast, where the lipid phosphonoacid is incorporated into liposomes, virtually all of the antiviral compound is incorporated into the liposome, and essentially none of the active compound is wasted.

The liposomes with the above formulations may be made still more specific for their intended targets with the incorporation of monoclonal antibodies or other ligands specific for a target. For example, monoclonal antibodies to the CD4 (T4) receptor may be incorporated into the liposome by linkage to phosphatidylethanolamine (PE) incorporated into the liposome by the method of Leserman, L. et al. (1980) *Nature* 288:602-604.

Therapeutic Use of the Lipid Derivatives

The dosage of 1-0-alkyl propanediol-3-phosphate prodrugs for a mammal, including a human, may vary depending upon the extent and severity of the condition that is treated and the activity of the administered compound. The dosage of the lipid prodrug is determined by reference to the recommended dosages of the active agent, bearing in mind that, in selecting the appropriate dosage in any specific case, consideration must be given to the patient's weight, general health, metabolism, age and other factors which influence response to the drug. Dosage levels for most commercially available therapeutic agents, as well as many agents that are being clinically investigated, are well established. For example, the dosage of AZT is reported to be from about 7 to about 21 mg/kg/day. The dosage of 1-O-octadecyl-propanediol-3-P-AZT, for example, can be from about 1 to 25 mg/kg/day, preferably about 4-8 mg/kg/day.

Formulations for oral ingestion are in the form of tablets, capsules, pills, ampoules of powdered active agent, or oily or aqueous suspensions or solutions. Tablets or other non-liquid oral compositions may contain acceptable excipients, vehicles, diluents, fragrances, or flavors known to the art for the manufacture of pharmaceutical compositions, to make the medication palatable or pleasing to use. The formulation can therefore include diluents, such as lactose or calcium carbonate; binding agents such as gelatin or starch; and one or more agents selected from the group consisting of sweetening agents, flavoring agents, coloring or preserving agents to provide a palatable preparation. Moreover, such oral preparations may be coated by known techniques to further delay disintegration and absorption in the intestinal tract.

Aqueous suspensions may contain the active ingredient in admixture with pharmacologically acceptable excipients, comprising suspending agents, such as methyl cellulose; and wetting agents, such as lecithin or long-chain fatty alcohols. The aqueous suspensions may also contain preservatives, coloring agents, flavoring agents and sweetening agents in accordance with industry standards. The preparations may further comprise antioxidants, such as ascorbic acid or tocopherol, and preservatives, such as $\alpha$-hydroxybenzoic acid esters.

The present invention is described below in detail using the following examples, but the chemical reactions described are disclosed in terms of their general application to the preparation of the lipid prodrugs of the invention. occasionally, the reaction may not be applicable as described to each compound included within the disclosed scope of the invention. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, or by routine modification of reaction conditions. Alternatively, other reactions disclosed herein or otherwise conventional will be applicable to the preparation of the corresponding compounds of the invention. In all preparative methods, all starting materials are known or readily preparable from known starting materials; all temperatures are set forth uncorrected in degrees Celsius; and, unless otherwise indicated, all parts and percentages are by weight.

It is believed that one skilled in the art can, using the preceding description, utilize the invention to its fullest extent. The following preferred embodiments are, therefore, to be construed as merely illustrative and not limitative for the remainder of the disclosure in any way whatsoever.

EXPERIMENTAL

In the experimental disclosure which follows, the following abbreviations apply: eq (equivalents); M (Molar); mM (millimolar); µM (micromolar); N (Normal); mol (moles); mmol (millimoles); µmol (micromoles); nmol (nanomoles); kg (kilograms); gm (grams); mg (milligrams); µg (micrograms); ng (nanograms); L (liters); mL (milliliters); µl (microliters); vol (volumes); and ° C. (degrees Centigrade).

Example 1

Preparation of Lipid Moieties Used in the Coupling Procedures (a) Synthesis of 1-O-alkyl-2-O-benzyl-sn-glycero-3-phosphatidic acid To a vigorously stirred solution of 1-octadecyl-2-benzyl glycerol (Bachem, Inc., Basel, Switzerland), hereinafter referred to as OBG, a mixture of pyridine, triethylamine and tetrahydrofuran (THF) was added. Neat phosphorous oxychloride, $POCl_3$, was added dropwise while maintaining the temperature between $-5°$ to $5°$ C. The reaction mixture was stirred for 90 minutes at a temperature of $4°$ C. The precipitated triethylamine hydrochloride was filtered and the residue treated with toluene at least twice (2×10 mL) and the solvent removed under reduced pressure. The resulting oil was converted to the ammonium salt upon careful addition of methanolic ammonium hydroxide. The yield was 55%, and the target compound was a white to pale yellow solid.

(b) Preparation of 1-O-octadecyl-1,3-propanediol

1-O-trityl-1,3-propanediol, synthesized according to the procedure of Sela, et al. (1987) *Nucleic Acids Research* 15:3124, was treated with octadecyl methanesulfonate (NuChek Prep, Inc.) in the presence of sodium hydride in dimethylformamide. The product, 1-O-octadecyl-3-O-trityl propanediol, was isolated and purified by flash chromatography. The trityl protecting group was removed by treatment with trifluoroacetic acid in dichloromethane to yield 1-O-octadecyl-1,3-propanediol. The compound was converted to the corresponding 3-phosphate by a procedure identical to the one in example (a).

(c) Synthesis of 1-O-octadecyl-2,2-dimethoxypropanediol-3-phosphate 2,2-Dimethoxypropanediol was synthesized according to the procedure of Cesarotti et al. (*Helv. Chim. Acta* 1993, 76, 2344).

To a solution of 2,2-dimethoxypropanediol (2.0 gm, 14.7 mmol) in dimethylformamide (100 mL) was added sodium hydride (9.7 gm, 17.6 mmol) and the mixture stirred at room temperature for 30 min. octadecyl methanesulfonate (5.63 gm, 16.2 mmol) was added as a solid in one portion, and the mixture was stirred at room temperature under an atmosphere of nitrogen gas overnight. The mixture was poured into ice-water (100 mL), upon which a solid separated. The solid was filtered off and dried. The solid was then dissolved in ethyl acetate and flash chromatographed over silica gel with 10% ethyl acetate in hexane as eluting solvent to yield pure product.

This product was converted to the 3-phosphate by the procedure used in example (a).

(d) N-tritylethanolamine

A mixture of ethanolamine, trityl chloride and pyridine was refluxed for 15 h. Water was added slowly to the cooled reaction and the precipitate collected by filtration. The crude product recrystallized from a 1:1 mixture of ethanol and water.

N-trityl-O-(1-O-octadecyl-2-benzyl-sn-glycero-3-phosphoryl)-ethanolamine

A mixture of 1, 2, and triisopropylbenzenesulfonyl chloride in pyridine was stirred at a temperature of 25° C. for a period of 24 h. The desired compound was extracted from the reaction mixture and detritylation was carried out by methods familiar to those skilled in the art.

Example 2

Coupling of 1-O-octadecyl-1,3-propanediol to a Phosphorylated Drug Derivative

I. Synthesis of 1-O-octadecyl-1,3-propanediol-3-P-Acyclovir

Preparation from ACV monophosphate and 1-O-octadecyl-1,3-propanediol

Acyclovir was phosphorylated by addition of phosphorous oxychloride ($POCl_3$). After 1-2 h at 0° C., acyclovir was extracted with ether as a phosphoryl dichloride. A 2N NaOH solution was added to an aqueous solution of the dichloride to bring the pH to about 9 to 10, converting the compound to the disodium form. Chromatography on Dowex 50 converted the disodium salt to acyclovir monophosphate. A solution of acyclovir monophosphate as its salt, such as tributylamine or trioctylamine, in pyridine was treated with batyl alcohol followed by triisopropylbenzenesulfonyl chloride (TIPS) at a temperature of 45° C., for a period of 28 h. The dark-colored solution was treated with water, followed by toluene, and the resulting solution was concentrated under reduced pressure. The crude product was purified by ion exchange chromatography followed by silica column chromatography to obtain the desired compound as a white chloroform-soluble powder in a yield of 50% with a purity >95%. In a similar manner, 1-O-octadecyl-2,2-dimethoxy-1,3-propanediol was coupled with acyclovir monophosphate to yield the corresponding acyclovir derivative.

II. Synthesis of 1-O-octadecyl-1,2-ethanediol-2-P-ara-C

A solution of cytosine arabinoside(ara-C)-5'-monophosphate (Sigma, St. Louis, Mo.), 1-O-octadecyl-1,2-ethanediol, and triisopropylbenzenesulfonyl chloride (TIPS) in pyridine was allowed to stir at a temperature of 45° C. over a period of 25 h. Water was added to the reaction mixture followed by toluene and the solvents removed under reduced pressure. The crude product was chromatographed on silica gel to afford the desired compound.

III: Preparation of 1-O-octadecyl-2-O-benzyl-sn-glycero-3-P-ara-C

The title compound can be prepared starting from 1-O-octadecyl-2-O-benzyl-sn-glycerol (OBG) as delineated in the preparation of II in which OBG can be used to couple with ara-C-monophosphate.

IV: Preparation of 1-O-octadecyl-2,2-dimethoxy-1,3-propanediol-3-P-ara-C

A solution of ara-C-monophosphate, 1-O-octadecyl-2,2-dimethoxy-1,3-propanediol and triisopropylbenzenesulfonyl chloride (TIPS) in pyridine was allowed to stir at a temperature of 45° C., over a period of 25 h. Water was added to the reaction mixture followed by toluene and the solvents removed under reduced pressure. The crude product was purified by silica chromatography to afford the desired compound with the desired purity.

Example 3

Coupling of Drugs having a Free Carboxyl Group to the Amino Group of a Monoglyceride Phosphorylethanolamine Preparation of the 1-O-Octadecyl-1,3-propanediol Derivative of Cefazolin 1-O-octadecyl-1,3-propanediol-3-phosphoethanolamine (1 mmol) and cefazolin (1.2 mmol, 3-[(5-methyl-1.3.-thiadiazol-2-yl)thio]-8-oxo-7](1H-tetrazol-1-yl)acetyl]amino]5-thia-1-azabicyclo[4.2.0]oct-2-ene-2-carboxylic acid) were dissolved in pyridine followed by N,N-dicyclohexylcarbodiimide (3 mmol, DCC). The reaction mixture was stirred for 24 h at 10° C. The reaction was stopped by the addition of cold water and the solvents were evaporated and the product was purified by preparative thin layer chromatography. The following compounds were similarly coupled to 1-O-octadecyl-1,3-propanediol-3-phosphoethanolamine by using the above procedure.

3a: ceftazidime {1-[7-(2-amino-4-thiazolyl)[1-carboxy-1-methylethyoxy)-imino]acetyl]amino]-2-carboxy-8-oxo-5-thia-1-azabicyclo[4.2.0]oct-2-en-3-yl]methyl]-Pyridinium hydroxide};

3b: Ceftiaxone {7-[2-amino-4-thiazoly)(methoxyimino) acetyl]amino]8-oxo-3-]1,2,5,6-tetrahydro-2-methyl-5,6-dioxo-1,2,4-triazin-3-yl)thio]methyl]-5-thia-1-azabicyclo [4.2.0]oct-2-ene-2-carboxylic acid}; and 3c: piperacillin {6-[[[[(4-ethyl-2,3-dioxo-1-piperazinyl) carbonyl]amino]phenylacetyl]amino]-3,3-dimethyl-7-oxo-4-thia-1-azabicyclo[3.2.0]heptane-2-carboxylic acid}.

Example 4

Coupling Drugs Containing a Free Amino Group to a 1-O-Octadecyl-1,3-propanediol-3-Phosphate Through an Aliphatic Chain Linker Preparation of 1-O-Octadecyl-1,3-propanediol-3-phosphate derivatives of cefazolin 4a: Hydroxycarboxylic Acid Linker Hydroxybutyric acid sodium salt (0.5 mol, Aldrich) was dissolved in methanol and dry HCl was passed to convert the acid to its methyl ester. Methanol was evaporated and the dry methyl ester linking compound was coupled to 1-O-octadecyl-1,3-propanediol-3-phosphate by using N,N'-dicyclohexylcarbodiimide (DCC) as a coupling agent. The resulting compound was subjected to a base-catalyzed methanolysis by using 0.5N methanolic sodium hydroxide and the free acid derivative was again coupled to various drugs containing free amino groups, such as, for example, the methyl ester of ceftazidime, or sulfamethazine as described above. The protective ester group was removed from the drug by treatment with base.

4b: Dihydroxyl Linker

In another embodiment, the carboxylic acid group of the linker was reduced to an alcohol group (after coupling to 1-O-octadecyl-1,3-propanediol-3-phosphate) to couple to free drugs having a free acid moiety.

Example 5

1-O-Octadecyl-2-O-benzyl-sn-glycero-3-phospho-Ara-C

5a: A solution of 1-O-octadecyl-2-O-benzyl-sn-glycero-3-phosphatidic acid (1) and ara-C in pyridine was treated with TIPS at a temperature of 40° C., over a period of 24 h. The reaction was stopped by addition of water and the solvent evaporated under reduced pressure. The crude product purified by chromatography to afford the title compound.

5b: Alternative preparation of this compound involved the coupling of OBG and ara-C monophosphate using pyridine as the solvent and TIPS as the coupling agent. Purification was effected using the standard procedures.

Using the above methods, the corresponding lipid derivatives of the following nucleoside analogs can be obtained:
5c: 2'-ara-fluoro-2-chlorodeoxyadenosine
5d: 5-fluorouridine
5e: 6-mercaptopurine riboside
5f: 3'-thia-dideoxycytidine
5g: 3'-thia-5-fluoro-dideoxycytidine
5h: Ganciclovir
5i: Acyclovir Example 6

Synthesis of 1-O-octadecyl-glycero-rac-3-phospho-5'-(3'-azido-3'-deoxy)thymidine Dry 1-O-octadecyl-rac-3-glycerol (batyl alcohol, 250 mg), 3'-azido-3'-deoxythymidine monophosphate sodium salt (0.725 gm) and 2,4,6,-triisopropylbenzenesulfonyl chloride (TIPS, 1.219 gm) were mixed in dry pyridine and chloroform overnight under nitrogen. Chloroform (50 mL) was added and the reaction mixture was washed twice with cold. 0.2N HCl and 0.2N sodium bicarbonate. The organic phase was removed in vacuo with a rotary evaporator and the product was crystallized at −20° C. from 20 mL of chloroform/acetone (12:8 by volume). The final purification of the compound was done by preparative thin layer chromatography using 500 micron layers of silica gel G developed with chloroform/methanol/concentrated ammonia/water (70/30/1/1 by volume).

Example 7

Synthesis of 1-O-Octadecyl-sn-glycero-3-Phosphonoformate

1-O-Octadecyl-2-O-benzyl-sn-glycerol (9.9 gm, 23 mmol) in dry pyridine (25 mL) was added dropwise to an ice-cold solution of ethoxycarbonyl phosphodichloridate (7.0 gm, 36 mmol) in dry chloroform (50 mL). The mixture was warmed to room temperature and stirred for 24 hours. The reaction was stopped by the addition of cold water (5 mL) and stirring for two hours. The reaction mixture was poured in water (100 mL) and the organic phase was separated. The aqueous phase was extracted chloroform (3×25 mL) and the organic extracts were combined. The combined organic phase was washed with aqueous saturated sodium chloride (50 mL), dried over anhydrous magnesium sulfate and concentrated in-vacuo to yield an oil. The oil was purified by flash chromatography with 10% methanol in chloroform as eluent to yield 1-O-octadecyl 2-O-benzyl-sn-glycero-3-ethylphosphonoformate as a colorless oil (6.2 gm, 46%).

A portion of the above oil (1.67 gm) was dissolved in absolute ethanol (100 mL), Pd/C (300 mg) were added and the mixture hydrogenated at 60 psi for 24 hours. The catalyst was filtered off to yield 1-O-octadecyl-sn-glycero-3-ethylphosphonoformate (11.0 gm, 71%)

To the ethylphosphonoformate (11.0 gm) in absolute. ethanol (50 mL) was added an aqueous solution of sodium hydroxide (8 mL, 1N) and the mixture stirred at room temperature for 30 minutes. The mixture was centrifuged and the solid isolated. The solid was washed with absolute ethanol (3×25 mL) and dried to give batyl phosphonoformate (0.7 gm).

Example 8

Coupling 1-O-octadecyl-1,3-propanediol-3-phosphatidic Acid (and compounds of example 1) to the Amino Group of a Peptide 1-O-octadecyl-1,3-propanediol-3-phosphatidic acid, (or any of the lipid-phosphate moieties) prepared as in Example 1 above, was partitioned between chloroform/methanol (2:1 (v/v); 200 mL) and cold 1N HCl (50 mL). The aqueous layer was re-extracted with chloroform methanol (2:1) (v/v); 100 mL). The combined organic phase was evaporated and dried under vacuum over $P_2O_5$. The resulting free phosphatidic acid was dissolved in a mixture of DMF (2 mL) and pyridine (2 mL) and to the solution was added the appropriate peptide having a free amino group (1 mmol) followed by N,N'-dicyclohexylcarbodiimide (DCC; Aldrich Chemical Co., Milwaukee, Wis., MW: 206, 620 mg, 3 mmol). The reaction mixture was stirred for 24 hours at room temperature. The solvents were evaporated and the product was purified by flash chromatography over silica gel column (2.5×50 cm) using a linear gradient of 0 to 50% methanol in chloroform. Fractions containing the desired product as indicated by TLC and HPLC were pooled and evaporated. The product was further purified, if necessary, by preparative HPLC or by crystallization yielding the 1-O-octadecyl-1,3-propanediol-3-phospho-(NH)-peptide. Any therapeutic peptide may be coupled in a like manner.

Example 9

Coupling 1-O-octadecyl-2-O-benzyl-3-phospho ethanolamine to the Amino Group of a Therapeutic Peptide Using Succinate as a Linking Group A solution of 1-O-octadecyl-2-O-benzyl-3-phosphatidic acid and ethanolamine in pyridine was treated with N,N'-dicyclohexylcarbodiimide and the mixture was allowed to stir at room temperature for a period of 24 h. The solvents were evaporated and the product purified by chromatography. Fractions containing the desired product were pooled and evaporated. The 1-O-octadecyl-2-O-benzyl-3-phosphoethanolamine was next treated with succinic anhydride to afford the hemisuccinate of 1-O-octadecyl-2-O-benzyl-3-phosphoethanolamine. The free carboxyl group of the hemisuccinate was coupled to the N-terminal amino group of a HIV protease inhibitor [D-Phe]-D-α-napthylalanine]-pipeolic acid-[α-OH-Leu]-Val amide (VST 7140) or a peptide such as VST 7194 or a renin inhibitor, enalkiren (A64662). Any therapeutically useful peptide may be coupled in a like manner.

Example 10

Coupling 1-O-alkyl-2-O-benzyl-sn-glycero-3-phosphatidic Acid to the Hydroxy Group of a Peptide 1-O-alkyl-2-O-benzyl-sn-glycero-3-phosphatidic acid (1 mmol) prepared as above was dissolved in a mixture of DMF (2 mL) and pyridine (2 mL) and to the solution was added the appropriate peptide having a free hydroxyl group (1 mmol). The reaction was carried out and the product was isolated as described in Example 9.

The condensation of the phosphatidic acid and the hydroxyl group of a peptide was also conveniently carried out by using 2,4,6-triisopropylbenzenesulfonyl chloride (TOS-Cl; Aldrich Chemical Co., Milwaukee, Wis.; MW: 302.86; 758 mg, 2.5 mmol) as a coupling agent in place of DCC.

Example 11

Coupling a Peptide Containing a Free Carboxyl Group 1-O-Octadecyl-1,3-propanediol-3-phosphoethanolamine A mixture of the appropriate peptide (1 mmol), and 1-O-octadecyl-1,3-propanediol-3-phosphoethanolamine (1 mmol) was dissolved in pyridine (5 mL) and DCC (3 mmol) followed by 1-hydroxybenzotriazole (HOBt; Aldrich Chemical Co., MW: 153; 450 mg, 3 mmol) were added. The reaction mixture was stirred for 24 hours at room temperature and the product was purified by silica gel chromatography as described in Example 1 followed by debenzylation as in Example 10. Any therapeutically useful peptide may be coupled in a like manner.

Example 12

Synthesis of Lipid Derivative of a Taxol Side Chain

Synthesis of β-(Benzoylamino)-α-(1-O-octadecyl-1,3-propanediol-3-phospho)-benzenepropanoate, ester (1)

To a solution of 1-O-octadecyl-1,3-propanediol-3-phosphate (0.5 mol) and β-(benzoylamino)-α-hydroxybenzenepropanoate ester either in an ethereal solvent like diethyl ether, tetrahydrofuran or a halogenated solvent like dichloromethane or chloroform was added DCC either neat or as a solution and allowed to stir for 2-25 h at a temperature of 4° C. Water was added to the reaction mixture and the solvents removed under reduced pressure. The crude product was chromatographed on silica gel to afford the desired compound.

Synthesis of β-(Benzoylamino)-α-((1-O-octadecyl-2-benzyl-sn-glycero-3-phospho)-benzenepropanoate ester (2)

A solution of 1-O-octadecyl-2-O-benzyl-sn-glycero-3-phosphatidic acid (0.1 mol) and β-(benzoylamino)-α-hydroxybenzenepropanoate ester in pyridine or chloroform was stirred in the presence of DCC (0.4 mol) at a temperature of 4° C. for a period of 6 h. Water was added to the reaction mixture and the contents extracted with chloroform. The solvent was removed under reduced pressure and the crude product purified by chromatography to afford the benzenepropanoate ester.

Example 13

Synthesis of β-amino Substituted Taxol Side Chain

Synthesis of β-Amino-α-(1-O-octadecyl-2-O-benzyl-sn-glycero-3-phospho)-benzenepropanoate ester To a solution of 1-O-octadecyl-2-O-benzyl-sn-glycero-3-phosphatidic acid (0.1 mol) and β-Amino-α-hydroxybenzene propanoate ester (0.1 mol) in chloroform or pyridine was added DCC (0.4 mol) and allowed to stir at a temperature of 4° C. for a period of 5 h. Water was added to the reaction mixture and the contents extracted with chloroform or other halogenated solvent. The solvent was removed under reduced pressure and the crude product purified by chromatography to afford the substituted ethanolamine of 1-O-octadecyl-2-O-benzyl-sn-glycero-3-phosphatidic acid.

Example 14

Hydrolysis of Propanoate Esters of Lipid Derivatized Taxol Side Chain

Synthesis of β-(Benzoylamino)-α-(1-O-alkyl-1,3-propanediol-3-phospho)-benzenepropanoic acid (3)

The propanoate ester (0.1 mol) from (1) was hydrolyzed using sodium methoxide in methanol or sodium carbonate in methanol at a temperature of 5° C. for a period of 4 h to afford the desired compound which is ready for coupling with baccatin III.

Synthesis of β-(Benzoylamino)-α-(1-O-octadecyl-2-O-benzyl-sn-glycero-3-phospho)-benzenepropanoic acid To a solution of 2 (0.1 mol) in methanol was added a solution of sodium methoxide in methanol and the resulting solution was stirred at a temperature of 5° C. for a period of 4 h. The reaction mixture was neutralized and the resulting solution concentrated under reduced pressure to afford the crude product. Purification by column chromatography gave the desired compound which is suitable for coupling with baccatin III or 10-deacetyl baccatin.

Example 15

Coupling of Lipid Derivative of Taxol Side Chain to Baccatin

A. Coupling of lipid derivative of phosophoethanolamine side chain to 10-deacetyl baccatin III.

To a solution of β-(benzoylamino)-α-(1-O-alkyl-1,3-propanediol-3-phospho)-benzenepropanoic acid (example 14) (0.1 mol) and 10-deacetyl baccatin III (0.1 mol) in chloroform was added DCC (0.4 mol) and allowed to stir at a temperature of 25° C. for a period of 7 h. Water was added to the reaction mixture and the contents extracted with chloroform. The organic layer was separated and the aqueous phase was extracted with chloroform. The combined organic layer was concentrated under reduced pressure and the crude product purified by chromatography to afford the 1-O-alkyl-1,3-propanediol-3-phosphoethanolamine derivative of taxol.

B. Coupling of 1-O-octadecyl-2-O-benzyl-3-phospho ethanolamine side chain to 10-deacetyl baccatin III.

To a solution of f-(benzoylamino)-α-(1-O-octadecyl-2-O-benzyl-sn-glycero-3-phospho)-benzenepropanoic acid (0.1 mol), 10-deacetyl baccatin III (0.1 mol) in chloroform was added DCC (0.4 mol) and allowed to stir at room temperature for a period of 10 h. Water was added to the reaction mixture and the contents extracted with chloroform. The organic layer was separated and the aqueous layer was extracted with chloroform. The combined organic layer was concentrated under reduced pressure and the crude product purified by chromatography to afford the batylbenzylphosphoethanolamine derivate of taxol.

In the preceding syntheses, proton NMR spectra were obtained with a General Electric QE-300 spectrometer, using tetramethylsilane as internal standard (key: s=singlet, d=doublet, t=triplet, q=quartet, dd=doublet of doublets, b=broad). UV spectra were recorded on Shimadzu UV-160, spectrophotometer. Fast atom bombardment mass spectra were determined by Mass Spectrometry Service Laboratory, University of Minnesota. Elemental analyses were determined by Galbraith Laboratories, Knoxville, Tenn. and Schwarzkopf Microanalytical Laboratory, NY. Melting points were obtained with a Fischer-Johns melting apparatus. Column chromatography was carried out on Merck silica gel 60 (70-230 mesh). Rf values were obtained with HPTLC Merck, Kieselgel 60 pre-coated plates, 10×10 cm. Anhydrous pyridine, 2,4,6-Triisopropylbenzenesulfonyl chloride (TIPS), and 3'-azido-3'-deoxythymidine (AZT) and 1,3-propanediol were purchased from Aldrich Chemical Co., Milwaukee, Wis. and 1-O-octadecyl-2-benzylglycerol was purchased from Bachem Bioscience Inc., Philadelphia, Pa.

Example 16

Single-Dose
1-O-octadecyl-sn-glycero-3-phospho-AZT Oral
Administration Compared to Continuous Oral AZT
Administration Treatment of Rauscher Leukemia Virus-Infected Mice:

Female BALB/C mice were infected with $1 \times 10^4$ plaque-forming units (PFU) of Rauscher leukemia virus complex (RLV) on day 0. Control animals were injected with saline. Beginning on day 2, groups of the infected mice as indicated in FIG. 1 were treated with AZT at doses from about 11.0 mg/kg/day to 15.0 mg/kg/day for 21 days either by offering AZT in drinking water or by gavaging with 1-O-octadecyl-sn-glycero-3-P-AZT once a day. On day 23 post-inoculation, the mice in both treatment protocols were sacrificed, and the spleen weights of the animals were determined. The mean spleen weights, indicating relative level of virus infection, for each dose level in the two protocols, are represented in the bar graphs of FIG. 1. The effective doses (ED50) of daily 1-O-octadecyl-sn-glycero-3-P-AZT given by a single oral administration and AZT given by oral administration in the drinking water were comparable.

It is apparent from the foregoing that other 1-O-alkyl-1,3-propanediol-3-phosphate derivatives and the other lipid adducts in Example 1 of therapeutic drugs can be substituted to obtain similar results of delivering a drug, otherwise poorly orally bioavailable, more effectively through the oral route. It should be further emphasized that the present invention is not limited to the use of any particular drug or therapeutic agent in the compounds of the invention; rather the beneficial results of the invention flow from the synthesis of the lipid moieties of Example 1 linked via a substituted or unsubstituted propanediol-3-phosphate, with or without a linker to these drugs and agents. Thus, regardless of whether a specific drug or agent is presently known, or whether it becomes known in the future, the methods of forming the presently contemplated lipid prodrugs therefrom are based on established chemical techniques, as will be apparent to those of skill in the art, and therefore these compounds are broadly enabled by the preceding disclosure. It should be emphasized again that the present syntheses are broadly applicable to formation of compounds from essentially all drugs having an appropriate structure, and the effectiveness of which can be improved by preparing a lipid prodrug form for use in the practice of the invention.

Example 17

Synthesis of 1-O-Octadecyl-2-O-methyl-sn-glycero-3-phospho-acyclovir

Acyclovir monophosphate (1 mmol) was converted to the tri-n-butylammonium salt (TBA) by treatment with tri-n-butylamine in methanol followed by lyophilization of the product. The TBA salt was dried by coevaporation with 10 mL pyridine twice. To a mixture of the dry acyclovir TBA salt and 1-O-octadecyl-2-O-methyl-sn-glycerol (1 mmol) in dry pyridine (20 mL) was added 2,4,6-triisopropylbenzene sulfonyl chloride (3 mmol), upon which the mixture turned bright yellow. The mixture was stirred at room temperature for 48 h, and quenched by addition of methanol (20 mL). The mixture was purified by flash chromatography over silica gel with an increasing gradient of methanol in dichloromethane as the eluting solvent. The appropriate fractions were pooled and concentrated in vacuo to yield the title compound as a colorless amorphous solid. Any pharmaceutically useful nucleoside analog monophosphate may be utilized as noted in the example to obtain the corresponding 1-O-alkyl, 2-O-methyl-sn-glycero-3-phosphate-analog, or other analogs thereof.

Example 18

Synthesis of
1-O-octadecyl-1,3-propanediol-3-phospho-acyclovir

Acyclovir monophosphate (1 mmol) was converted to the tri-n-butylammonium salt (TBA) by treatment with tri-n-butylamine in methanol followed by lyophilization of the product. The TBA salt was dried by coevaporation with 10 mL pyridine twice. To a mixture of the dry acyclovir TBA salt and 1-O-octadecyl-1,3-propanediol (1 mmol) in dry pyridine (20 mL) was added 2,4,6-triisopropylbenzene sulfonyl chloride (3 mmol), upon which the mixture turned bright yellow. The mixture was stirred at room temperature for 48 h, and quenched by addition of methanol (20 mL). The mixture was purified by flash chromatography over silica-gel with an increasing gradient of methanol in dichloromethane as the eluting solvent. The appropriate fractions were pooled and concentrated in vacuo to yield the title compound as an amorphous solid. Any pharmaceutically useful nucleoside analog monophosphate may be utilized as noted in the example to obtain the corresponding 1-O-alkyl, 2-O-methyl-sn-glycero-3-phosphate-analog.

Example 19

1-O-Octadecyl-2-O-methyl-sn-glycero-3-phospho-ethanolamine-Peptide 7194 (HIV Protease inhibitor) conjugated through the C-terminus Pentapeptide 7194, with a tert-butyloxycarbonyl protecting group at the N-terminus (t-BOC-L-Phe-[B-D-NAL]-PIP—[a-OH-Leu]-Val-COOH) (2 mmol) was mixed with 1-O-octadecyl-2-O-methyl-sn-glycero-3-phosphoethanolamine (2 mmol) in dry pyridine (50 mL) and cooled in an ice-salt bath. A solution of dicyclohexylcarbodiimide (6 mmol) in dry dichloromethane was added to the mixture dropwise with stirring. The resulting mixture was allowed to stir at room temperature overnight. The reaction mixture was filtered and the filtrate was concentrated to dryness in vacuo. The residue was purified by silica gel flash chromatography with an increasing gradient of methanol in chloroform as the eluent to yield the title compound, with the t-BOC protecting group at the N-terminus of the peptidyl moiety. The protecting group was removed by treatment with 10% trifluoroacetic acid in dichloromethane to yield title compound. Any pharmaceutical peptide drug having a tert-butyloxycarbonyl protecting group at the N-terminus may be converted to the corresponding 1-O-octadecyl-2-O-methyl-sn-glycero-3-phosphoethanolamine analog using the method described above.

Example 20

1-O-Octadecyl-2-O-methyl-sn-glycero-3-phospho-L-Peptide 7194 (HIV Protease inhibitor) conjugated through the N-terminus: (L—O—CH$_2$CH$_2$—COO—):

Pentapeptide 7194, as its methyl ester at C-terminus (2 mmol) was mixed with 3-hydroxy propanoic acid (2 mmol) in dry dichloromethane (50 mL). The mixture was cooled in an ice-salt bath and N N-dicyclohexylcarbodiimide (2.4 mmol) was added. The mixture was stirred at 0° C. for 3 h and at room temperature overnight. The mixture was filtered and the filtrate was concentrated to dryness in vacuo. The residue was flash chromatographed over silica gel with an increasing gradient of methanol in dichloromethane as the eluting solvent to obtain pure product as a foam.

To a mixture of the above foam (1 mmol) and 1-O-octadecyl-2-O-methyl-sn-glycero-3-phosphatidic acid (1 mmol) in dry pyridine (50 mL), cooled in an ice-salt bath, was added a solution of dicyclohexylcarbodiimide (3 mmol) in dry dichloromethane dropwise with stirring. The mixture was allowed to stir at room temperature overnight. The resulting reaction mixture was filtered and the filtrate was concentrated to dryness in vacuo. The residue was purified by silica gel flash chromatography with an increasing gradient of methanol in chloroform as the eluent to yield the title compound as the methyl ester at the C-terminus. The ester was treated with ethanolic sodium hydroxide to yield title compound. Similarly, any pharmaceutical peptide drug having a methyl ester at the C-terminus may be converted to the corresponding 1-O-octadecyl-2-O-methyl-sn-glycero-3-phosphate-analog using the method of this example.

Example 21

General Method of Synthesis of 1-O-Octadecyl-2-O— methyl-sn-glycero-3-phospho-5'-oligonucleotides To the fully protected oligonucleotide attached to the solid support on a DNA synthesis column, and having a free 5'-hydroxyl group (1 μmol) was added a mixture of 1-O-octadecyl-2-O-methyl-sn-glycero-3-phosphatidic acid (5 μmol) and dicyclohexylcarbodiimide (5 μmol) in pyridine (2 mL). The reaction was allowed to proceed at room temperature overnight.

The column with the derivatized oligonucleotide was washed with pyridine (2 mL) and acetonitrile (2 mL). Iodine in tetrahydrofuran (0.1M, 1 mL) was added to the column over 5 mins. The lipid-oligonucleotide was freed from the solid support by the addition of ammonia, and deblocked completely by treatment with ammonia at 55° C. overnight. The resulting 1-O-octadecyl-2-O-methyl-sn-glycero-3-phospho-5'-oligonucleotide was purified by HPLC to yield pure compound. oligonucleotides having from 2-24 bases may be derivatized in this manner, using any of the lipid-phosphate moieties in Example 1.

Example 22

Synthesis of 1-O-octadecyl-2-O-methyl-sn-glycero-3-phospho-ganciclovir

Ganciclovir monophosphate (1 mmol) was converted to the tri-n-butylammonium salt (TBA) by treatment with tri-n-butylamine in methanol followed by lyophilization of the product. The TBA salt was dried by coevaporation with 10 mL pyridine twice. To a mixture of the dry ganciclovir TBA salt and 1-O-octadecyl-2-O-methyl-sn-glycerol (1 mmol) in dry pyridine (20 mL) was added 2,4,6-triisopropylbenzene sulfonyl chloride (3 mmol), upon which the mixture turned bright yellow. The mixture was stirred at room temperature for 48 h, and quenched by addition of methanol (20 mL). The mixture was purified by flash chromatography over silica gel with an increasing gradient of methanol in dichloromethane as the eluting solvent. The appropriate fractions were pooled and concentrated in vacuo to yield the title compound as a colorless amorphous solid.

Example 23

Synthesis of 1-O-octadecyl-1,3-propanediol-3-phospho-ganciclovir

Ganciclovir monophosphate (1 mmol) was converted to the tri-n-butylammonium salt (TBA) by treatment with tri-n-butylamine in methanol followed by lyophilization of the product. The TBA salt was dried by coevaporation with 10 mL pyridine twice. To a mixture of the dry ganciclovir TBA salt and 1-O-octadecyl-1,3-propanediol (1 mmol) in dry pyridine (20 mL) was added 2,4,6-triisopropylbenzene sulfonyl chloride (3 mmol), upon which the mixture turned bright yellow. The mixture was stirred at room temperature for 48 h, and quenched by addition of methanol (20 mL). The mixture was purified by flash chromatography over silica gel with an increasing gradient of methanol in dichloromethane as the eluting solvent. The appropriate fractions were pooled and concentrated in vacuo to yield the title compound as an amorphous solid.

Example 24

1-O-Octadecyl-2,2-dimethoxy-1,3-propanediol-3-phosphonoformate, disodium salt:

To a solution of 1-O-octadecyl-2,2-dimethoxy-1,3-propanediol (1.92 gm, 5 mmol) and ethyl phosphonoformate (1.19 g, 5 mmol) in dry pyridine (50 mL), cooled in an ice-salt bath, was added a solution of N,N-dicyclohexylcarbodiimide (3.1 g, 15 mmol) in dry dichloromethane (20 mL). The resulting mixture was stirred at room temperature over. The mixture was filtered, and the filtrate was concentrated to dryness. The residue was flash chromatographed with a gradient of 0-10% methanol in dichloromethane to give the target compound. In a similar manner, use of ethyl phosphono-acetate resulted in the corresponding 1-O-octadecyl-2,2-dimethoxy-1,3-propane diol-3-ethylphosphonoacetate.

A suspension of 1-O-octadecyl-2,2-dimethoxy-1,3-propanediol-3-phosphonoformate (0.91 gm, 1.7 mmol) in absolute ethanol (20 mL) was treated with 1N aqueous sodium hydroxide (3.8 mL)-, and the resulting mixture stirred at room temperature for 1.5 h. The mixture was centrifuged, the resulting solid suspended in absolute ethanol (20 mL). The suspension was vortexed and centrifuged. The solid was dried to yield product as an amorphous powder (0.9 gm). In a similar manner, the corresponding phosphonoacetate derivative was synthesized.

Example 25

1-O-Octadecyl-2-O-benzyl-sn-glycero-3-phosphonoformate, Disodium Salt

1-O-Octadecyl-2-O-benzyl-sn-glycerol (1 mmol) and ethyl phosphonoformate (1 mmol) were dissolved in pyridine (20 mL). The solution was cooled in an ice-salt bath and N,N-dicyclohexylcarbodiimide (2.4 mmol) in dichloromethane was added. The mixture was stirred at 0° C. for 3 h and at room temperature overnight. The mixture was filtered and the filtrate was concentrated to dryness in vacuo. The residue was flash chromatographed over silica gel with an increasing gradient of methanol in dichloromethane as the eluting solvent to obtain pure product as a foam.

A suspension of the above foam (2 mmol) in absolute ethanol (20 mL) was treated with 1N aqueous sodium hydroxide (40.1 mL), and the resulting mixture stirred at room temperature for 1.5 h. The mixture was centrifuged, the resulting solid suspended in absolute ethanol (20 mL). The suspension was vortexed and centrifuged. The solid was dried to yield product as an amorphous powder.

Example 26

1-O-Octadecyl-1,3-propane diol-3-phosphonoformate, Disodium Salt

1-O-Octadecyl-1,3-propanediol (1.41 gm, 4 mmol) and ethyl phosphonoformate (1.19 gm, 5 mmol) were dissolved in pyridine (20 mL). The solution was cooled in an ice-salt bath and N,N-dicyclohexylcarbodiimide (2.4 mmol) in dichloromethane was added. The mixture was stirred at 0° C. for 3 h and at room temperature overnight. The mixture was filtered and the filtrate was concentrated to dryness in vacuo. The residue was flash chromatographed over silica gel with an increasing gradient of methanol in dichloromethane as the eluting solvent to obtain 1-O-octadecyl-1,3-propane diol-3-ethyl phosphonoformate (1.15 gm, 62%) as an amorphous powder.

A suspension of the ethyl phosphonoformate ester (0.8 gm, 1.72 mmol) in absolute ethanol (20 mL) was treated with 1N aqueous sodium hydroxide (4.3 mL), and the resulting mixture stirred at room temperature for 1.5 h. The mixture was centrifuged, the resulting solid suspended in absolute ethanol (20 mL). The suspension was vortexed and centrifuged. The solid was dried to yield title compound II (0.64 gm, 77%) as an amorphous powder.

Example 27

1-O-Octadecyl-2,2-dimethoxy-1,3-propane diol-3-phospho-Acyclovir

To a solution of 1-O-octadecyl-2,2-dimethoxy-1,3-propanediol (1.92 gm, 5 mmol) and ethyl phosphonoformate (1.5 gm, 5 mmol) in dry pyridine (50 mL), cooled in an ice-salt bath, was added a solution of N,N-dicyclohexylcarbodiimide (3.1 gm, 15 mmol) in dry dichloromethane (20 mL). The resulting mixture was stirred at room temperature over. The mixture was filtered, and the filtrate was concentrated to dryness.

The residue was flash chromatographed with a gradient of 0-10% methanol in dichloromethane to give the target compound. In a similar manner, use of Ganciclovir monophosphate resulted in the corresponding 1-O-octadecyl-2,2-dimethoxy-1,3-propanediol-3-phospho-Ganciclovir.

Example 28

Synthesis of 1-0-alkyl-2-halo-sn-glycero-3-phospho-Acyclovir and 1-0-alkyl-2-amino-sn-glycero-3-phospho-Ganciclovir The stereo-controlled synthesis of 1-0-alkyl-2-halo-sn-glycero-3-phospho-Acyclovir is outlined in Scheme I. 2,3-Isopropylidene-sn-glycerol, upon treatment with the appropriate alkylmethane sulfonate, leads to the intermediate 2. Removal of the isopropylidene group by treatment with acetic acid followed by tritylation with trityl chloride and pyridine results in compound 3, with a free 2-hydroxyl group. Treatment of 3 with n-halosuccimide and triphenyl phosphine according to the procedure of Bose and Lal (1973, *Tetrahedron Lett.* 40:3937) will lead to intermediate 4. The replacement of the hydroxyl group with halogen proceeds with complete inversion (SN2 displacement) and in yields from 65-95%. Removal of the trityl-group with trifluoroacetic acid in dichloromethane leads to the halo compound 5. Reaction of 5 with Acyclovir monophosphate and dicyclohexylcarbodiimide in pyridine will lead to the target compound.

While this procedure works when X is Cl, Br and I, a slightly different approach is needed for the analog when X is F. Treatment of the intermediate 3 with diphenyltrifluorophosphorane according to a procedure reported by Kobayashi and coworkers (1968, *Chem. Pharm. Bull.* 16(9):1784) leads to the conversion of alcohol 3 to the fluorinated compound 4 in good yields. Subsequent steps to the fluoro analogs are identical to those described earlier.

Treatment of bromo intermediate 4 described in Scheme I with liquid ammonia in a steel bomb will result in amination at the 2-position. Treatment of the resulting 2-amino compound with benzyl bromide will protect the 2-amino group. Subsequent steps will be identical to those described in Scheme 1 up to intermediate 1-0-alkyl-2-benzylamino-snglycero-3-phospho-Ganciclovir. The benzyl protecting group can be removed at this point by hydrogenolysis with Pd/C to give the target compound.

Treatment of the amino intermediate with acyl chloride will result in the N-acyl compound.

Alternatively, treatment of the bromo intermediate 4 with mono or dialkyl amine will result in the monoalkyl amino and dialkylamino derivatives.

The procedures described above can be carried out with readily available starting materials, the methodology is well documented and those skilled in the art can recognize the modifications needed in starting materials and methods to synthesize the 2-amino analogs that have been listed.

Example 29

Synthesis of Thiophosphonoacids and Their Lipid Prodrugs

Thiophosphonoformic acid is synthesized according to the procedure of McKenna (U.S. Pat. No. 5,072,032) by the reaction of trimethyl phosphonoformic acid with Lawesson's reagent [2,4-bis(4-methoxyphenyl)-1,3-dithia-2,4-diphosphetane 2,4 sulfide]. Thiophosphonoacetic acid is also synthesized in a similar manner.

Selenophosphonoformic acid can be synthesized by treatment of trimethylphosphonoformic acid with elemental selenium by adaptation of procedures reported by Stec and coworkers (1976, Stec, W. J., Okruszek, A. and Michalski, J., *J. Org. Chem.* 41, 233), and by Buina et al. (1979, Buina, N. A.; Sibgatullina, F. G.; Neureldinor, I. A., *Izv. Akad. Nauksssr.*, Ser. Khim. 10, 2362). Selenophosphonoacetic acid can also be synthesized in a similar manner. The selenoacids can then be converted to the corresponding lipid prodrugs by procedures identical to those for the oxo- and thio-analogs.

The synthesis of 1-O-octadecyl-1,3-propanediol-3-thiophosphonoformic acid was carried out in a manner similar to the synthesis of 1-O-octadecyl-1,3-propanediol-3-phosphonoformic acid, with some modifications. 1-O-octadecyl-1,3-propanediol was coupled to thiophosphonoformic acid ethyl ester using dicyclohexylcarbodiimide. After purification by silica gel chromatography, the target compound was obtained by base hydrolysis of the ester. 1-O-octadecyl-1,3-propanediol-3-thiophosphonoacetic acid was synthesized in a similar manner, as were 1-O-octadecyl-2,2-dimethoxy-1,3-propanediol-3-thiophosphonoformate and the corresponding thiophosphonoacetate.

Example 30

Synthesis of 1-O-octadecyl-1,2-ethanediol-2-phosphonoformate

To a solution of carbethoxyphosphodichloridate (1.6 mmol) in chloroform (25 mL), cooled to 0° C. in an ice salt bath, was added a solution of 1-O-octadecylethanediol (1 mmol) in pyridine (15 mL), dropwise with stirring. The mixture was allowed to warm to room temperature and stirred at room temperature overnight. The mixture was cooled, and 1 mL water was added. After stirring at 0° C. for 2 h, the mixture was concentrated in vacuo. The residual oil was flash chromatographed with chloroform-methanol 95:5 as eluent to yield product: 1-O-octadecylethanediol-2-ethylphosphonoformate.

The ethyl ester was dissolved in 1:1 mixture of ethanol and 0.1N NaOH (50 mL) and sonicated for 15 minutes. The resulting mixture was stirred at 60° C. in an oil bath for 2 h. The mixture was filtered and the filtrate was concentrated to dryness in vacuo. The resulting solid was resuspended in water, cooled and lyophilized to yield target compound.

Example 31

Synthesis of 1-O-octadecyl-2-O-methyl-sn-glycero-3-phosphonoformate

To a solution of carbethoxyphosphodichloridate (1.6 mmol) in chloroform (20 mL), cooled to 0° C. in an ice salt bath was added a solution of 1-O-octadecyl-2-O-methyl-sn-glycerol (11.0 mmol) in pyridine (15 mL) dropwise. The mixture was stirred at room temperature overnight. The mixture was cooled, 2 mL of water added and the resulting mixture stirred at room temperature for 2 h. The reaction mixture was then concentrated in vacuo, and the residue was flash chromatographed over silica gel with chloroform:methanol as eluent.

The ethyl ester was dissolved in a 1:1 mixture of ethanol and 0.1N NaOH and sonicated for 15 minutes. The mixture was heated with stirring at 60° C. for 2 h, filtered and the filtrate evaporated to dryness. The residue was recrystallized from 25% aqueous ethanol to yield pure product.

Example 32

Synthesis of Nucleoside Analog Species Wherein X=CH—OH, m=1, R1=octadecyl (Compound #8 on Scheme II)

D-erythrose, 1 (purchased from Aldrich Chemical Company), upon treatment with NaH and benzyl bromide in DMF at −70° C. will give the selectively protected species 4-O-benzyl-erythrose, 2. Treatment of this intermediate with dimethoxypropane and acetone with trace amounts of perchloric acid will lead to 2,3-di-O-isopropylidene-4-O-benzyl erythrose 3. Reduction of compound 3 with sodium borohydride leads to the protected erythritol, 4. Treatment of 4 with octadecylmethanesulfonate yields the 1-O-octadecyl-2,3,di-O-isopropylidene-4-O-benzylerythritol 5. Debenzylation with Pd/C and hydrogen followed by DCC coupling with a nucleoside analog monophosphate will yield intermediate 7. Deblocking of 1 with 10% TFA in $CH_2Cl_2$ followed by base hydrolysis yields target compound 8.

Example 33

Synthesis of Nucleoside Analog Derivatives Wherein R2=H, X=CH—OH, R=octadecyl, m=2 (compound 17 on Scheme III)

Commercially available D-ribose, 9, (Sigma Chemical Co.) upon treatment with trimethylsilyl methylmercaptan by adaptation of a procedure by Evans and Co-workers (Evans, D. A., Truesdale, L. K., Gimm, K. G., Nesbitt, S. L., *J. Am. Chem. Soc.* 99, 5009, 1977) will result in the dimethyldithioacetal 10. This locks the ribose in the open chain conformation. Treatment of the protected ribose with benzyl bromide in DMF at −70° C. will result in selective blocking of the 5-primary hydroxyl group of ribose leading to compound II. Such selective blocking has been reported in the literature (1987, Yukuzawa, A., Sato, H., Masamune, T., Tetrahedron Lett. 28, 4303). The 2, 3, and 4 hydroxyl groups on the 1,5 derivatized ribose can be protected by treatment with methoxymethyl chloride (1972, Stark, G., Takashi, T., *J. Am. Chem. Soc.* 94, 7827) to yield the fully protected ribose intermediate 12.

The aldehyde at the C position is regenerated by treatment of intermediate 12 with $AgNO_3/Ag_2O$ (1977, Corey, E. J., Shibasaki, M., Knolle, J., Sugahara, T., *Tetrahedron Lett.* 785) to yield compound 13. Reduction with sodium borohydride followed by alkylation with octadecylmethanesulfonate yields the 1-O-octadecyl-2,3,4-tri-O-methoxymethyl-5-O-benzyl ribose 15.

Removal of the benzyl group by hydrogenation with Pd/C followed by coupling with nucleoside analog phosphate using dicyclohexylcarbodiimide yields the intermediate 16. Treatment with acetic acid removes the methoxymethyl protecting groups and leads to the target compound, 17.

Example 34

1-S-Octadecyl-1-thiopropane-3-phospho-Acyclovir

To a stirred mixture of 3-mercapto-1-propanol (10.0 gm, 0.11 mol) and dry DMF (400 mL) was added sodium hydride (3.6 gm, 0.15 mol). When hydrogen evolution ceased, octadecylmethanesulfonate (35.9 gm, 0.11 mol) was added. Stirring was continued 2 hours then the mixture was poured into crushed ice (500 gm). The precipitated product was collected by vacuum filtration, washed with methanol (100 mL) and dried to give 1-S octadecyl-1-thio-3-propanol (24.2 gm, 64%).

1-S-Octadecyl-1-thio-3-propanol (0.3 gm, 0.9 mmol) and acyclovir monophosphate 0.30 gm, 1.0 mmol) were dissolved in pyridine (20 mL) and stirred. The solution was cooled in an ice-salt bath and N,N-dicyclohexylcarbodiimide (0.56 gm, 2.7 mmol) in dichloromethane (10 mL) was added. The mixture was stirred at. 0° C. for 3 hours and at room temperature overnight. The mixture was filtered and the filtrate was concentrated to dryness in vacuo. The residue was flash chromatographed over silica gel with an increasing gradient of methanol in dichloromethane as the eluting solvent to obtain 1-S-octadecyl-1-thiopropane-3-phospho-Acyclovir as a white solid.

Example 35

Human Cytomegalovirus (HCMV) Antiviral Susceptibility Assay

Subconfluent MRC-5 cells in 24-well culture dishes were pretreated for 24 hours with various concentrations of drug in MEM medium containing 2% FBS and antibiotics. The media was removed and virus added at a dilution that will result in a 3-4+ cytopathic effect (CPE) in the no-drug wells in five days. This was absorbed for 1 hour at 37° C., aspirated and replaced with the drug dilutions. After five days of incubation HCMV DNA was quantified in triplicate by nucleic acid hybridization using a CMV AntiviraL Susceptibility Test Kit from Diagnostic Hybrids, Inc. (Athens, Ohio). The media was removed and cells lysed according to the manufacturer's instructions.

After absorption of the lysate, the Hybriwix™ filters were hybridized overnight at 60° C. The Hybriwix™ were washed for 30 minutes at 73° C. and counted in a gamma counter. The results are expressed as HCMV DNA as a percentage of the untreated HCMV-infected control cells.

TABLE I

ANTI-HUMAN CYTOMEGALOVIRUS ACTIVITY OF PHOSPHONOFORMIC ACID AND VARIOUS PRODRUGS

| COMPOUND | $IC_{50}$, µM M ± SD | FOLD INCREASE IN ACTIVITY | p VALUE |
|---|---|---|---|
| PFA | 46 ± 19 (4) | — | — |
| B-PFA | 0.43 ± 0.27 (9) | 107 | <0.0001 |
| BB-PFA | 0.54 ± 0.65 (8) | 72 | <0.0001 |
| MB-PFA | 0.64 ± 0.14 (3) | 72 | 0.0050 |
| ODDMOP-PFA | 0.22 ± 0.14 (2) | 209 | — |

ABBREVIATIONS: PFA, phosphonoformate; B-PFA, 1-O-octadecyl-sn-glycero-3-phosphonoformate; BB-PFA, 1-O-octadecyl-2-O-benzyl-sn-glycero-3-phosphonoformate; and MB-PFA, 1-O-octadecyl-2-O-methyl-sn-glycero-3-phosphonoformate; ODDMOP-PFA, 1-O-octadecyl-2,2-dimethoxypropane-3-phosphonoformate.

The compounds of this invention are all substantially more active than the free drug, PFA. MB-PFA and BB-PFA are equivalent in antiviral activity to B-PFA while ODDMOP—PFA is substantially more active.

Example 36

HSV Antiviral Susceptibility Assay

Subconfluent MRC-5 cells in 24-well culture dishes were inoculated by removing the media and adding HSV-1 virus at a dilution that will result in a 3-4+CPE in the no-drug well in 20-24 hours. This was absorbed for 1 hour at 37° C., aspirated and replaced with various concentrations of drugs in MEM medium containing 2% FBS and antibiotics. After approximately 24 hours of incubation, HSV DNA was quantified in triplicate by nucleic acid hybridization using a HSV Antiviral Susceptibility Test Kit from Diagnostic Hybrids, Inc. (Athens, Ohio). The media was removed and cells lysed according to the manufacturer's instructions. After absorption of the lysate, the Hybriwix™ filters were hybridized overnight at 60° C. The Hybriwix™ were washed for 30 minutes at 73° C. and counted in a gamma counter. The results are expressed as a percentage of the untreated HSV-infected control cells.

TABLE II

INHIBITION OF HUMAN HERPES SIMPLEX VIRUS 1 REPLICATION BY PHOSPHONOFORMATE AND PHOSPHONOFORMATE PRODRUGS

| COMPOUND | $IC_{50}$, µM (n) | FOLD INCREASE IN ACTIVITY | p VALUE |
|---|---|---|---|
| PFA | 47 ± 20 (6) | — | — |
| B-PFA | 1.1 ± 1.1 (5) | 43 | 0.0003 |
| BB-PFA | 1.4 ± 0.4 (4) | 34 | 0.0003 |
| MB-PFA | 0.65 ± 0.21 (4) | 72 | 0.0009 |

ABBREVIATIONS: PFA, phosphonoformate; B-PFA, 1-O-octadecyl-sn-glycero-3-phosphonoformate; BB-PFA, 1-O-octadecyl-2-O-benzyl-sn-glycero-3-phosphonoformate; MB-PFA, 1-O-octadecyl-2-O-methyl-sn-glycero-3-phosphonoformate.

All compounds of the invention are more active than free PFA. MB-PFA appears to more active than B-PFA.

Example 37

Plaque Reduction Assay for HIV-1 Replication in HT4-6C Cells

HT4-6C cells and plaque reduction assay, CD4-expressing HeLa cells, HT4-6C cells (Chesebro, B. and K. Wehrly (1988) *J. Virol.* 62:3779-3788), were obtained from Bruce Chesebro, Hamilton, Mont. The effect of antiviral compounds on HIV replication was measured by a plaque reduction assay. Briefly, monolayers of HT4-6C cells were infected with 100 to 300 PFU of virus per well in 24-well microdilution plates. Various concentrations of drug were added to the culture medium, Dulbecco's Modified Eagle Medium containing 5% fetal bovine serum and antibiotics, as noted above. After 3 days at 37° C., the monolayers were fixed with 10% formaldehyde solution in phosphate-buffered saline and stained with 0.25% crystal violet to visualize virus plaques (Larder, B. et al. (1989) *Science* 243:1731-1734). Antiviral activity was assessed as the percentage of control Plaques measured in drug-treated samples.

TABLE III

ANTIVIRAL EFFECT OF PHOSPHONOFORMATE AND PHOSPHONOFORMATE PRODRUGS ON HUMAN IMMUNODEFICIENCY VIRUS-1 REPLICATION IN HT4-6C CELLS

| COMPOUND | $IC_{50}$, µM (n) | FOLD INCREASE IN ACTIVITY | p VALUE |
| --- | --- | --- | --- |
| PFA | 133 ± 54 (8) | — | — |
| B-PFA | 3.60 ± 1.51 (3) | 37 | 0.0015 |
| BB-PFA | 14.8 ± 7.3 (2) | 9.0 | 0.0091 |
| MB-PFA | 1.28 ± 0.73 (4) | 104 | 0.0014[1] |

[1] p = 0.0373 versus B-PFA

All compounds of this invention are more active than PFA. MB-PFA is significantly more active than B-PFA and BB-PFA.

Example 38

Synthesis of Radiolabeled Compounds and Pharmacokinetic Studies in Mice

A. Synthesis of 1-O-octadecyl-2-O-methyl-sn-glycero-3-[$^{14}$C]-PFA 2.5 mCi (0.083 mmol) of ethoxy[14C]carbonylphosphonic dichloride (30 µCi/µmol) in 0.5 mL chloroform was cooled to 0° C. 23 mg (0.064 mmol) of 1-O-octadecyl-2-O-methyl-sn-glycerol in 1.5 mL of chloroform/pyridine (2:1) at 0° C. was added while stirring. After 18 hours at room temperature the reaction was stopped with 0.5 mL of water and the mixture dried under nitrogen. The sample was dissolved in 80:20:1:1 (C/M/NH$_4$/W) and loaded onto a 1 gm silica gel column (70-230 mesh) which was eluted with the same solvent. Fractions containing the ethylester of 1-O-octadecyl-2-O-methyl-sn-glycero-3-PFA were pooled and dried under nitrogen. Half of the ethyl ester was deblocked by dissolving in 1 mL of 50% ethanol and adding 24 µmol of NaOH. The mixture was dried and redissolved in 1 mL of 50% ethanol and again dried under nitrogen. The deblocked product was dissolved in 80:20:1:1 and loaded onto a 1g silica column, washed with 5 mL of 80:20:1:1 and eluted with 15 mL of 70:58:8:8. The fractions containing the purified product were pooled, dried under nitrogen and redissolved in C/M/W (2:3:1). The final yield was 7%. The specific activity is assumed to have remained at 30 µCi/µmol.

B. Synthesis of 1-O-Octadecyl-sn-glycero-3-[$^{14}$C]-PFA 5 mCi (0.167 mmol) of ethoxy[$^{14}$C]carbonylphosphonic dichloride (30 µCi/µmol) in 1 mL chloroform was added to 87 mg (0.2 mmol) of 1-O-octadecyl-2-O-benzyl-sn-glycerol in 1.5 mL of chloroform/pyridine (2:1) stirring at 0° C. After 18 hours at room temperature the reaction was stopped with 0.5 mL of water and the mixture dried under nitrogen. The sample was dissolved in 3.5 mL ethanol and placed in a hydrogenation vessel overnight at 60 psi hydrogen with 10% palladium on carbon. The process was repeated with the addition of 10% palladium hydroxide on carbon. The catalyst was removed and the sample dried under nitrogen. The sample was redissolved in 80:20:1:1 (C/M/NH$_4$/W) and loaded onto a 5 gm silica gel column (70-230 mesh) which was eluted with the same solvent. The purest fractions containing the ethyl ester of Batyl-PFA were pooled and dried under nitrogen. Half of the ethyl ester was deblocked by dissolving in 2 mL of 50% ethanol and adding 50 µmol (2.5 eq) of NaOH. The mixture was dried and redissolved in 2 mL of 50% ethanol and again dried under nitrogen. The deblocked product was dissolved in 80:20:1:1 and eluted with 20 mL of 70:58:8:8. The fractions containing the purest product were pooled, dried under nitrogen and redissolved in 2 mL of C/M/W (2:3:1). The final yield was 2.5%.

C. Oral Administration of $^{14}$C—PFA Lipid Prodrugs to Mice

1-O-Octadecyl-sn-glycero-3-PFA[$^{14}$C] and 1-O-octadecyl-2-O-methyl-sn-glycero-3-PFA[$^{14}$C] (30 microcuries/micromole) were dried with dioleoylphosphatidylcholine/cholesterol/drug in a molar ratio of 60/30/10 in a nitrogen stream, lyophilized overnight and isotonic sorbitol was added. After vortexing and warming, the vessel was sonicated at maximum output in a Heat Systems cup and horn sonicator for one hour. The resulting liposome preparation was filtered through a 0.2 micron filter and administered to mice by oral gavage in a dose of 20 mg/kg of the respective PFA lipid prodrugs. After 24 hours the animals were sacrificed and tissues removed, blotted dry, weighed and homogenized. Aliquots were counted and the amount of radioactivity determined. The results are expressed as nanomoles of lipid prodrug PFA[$^{14}$C] per gm tissue.

Figure 2:
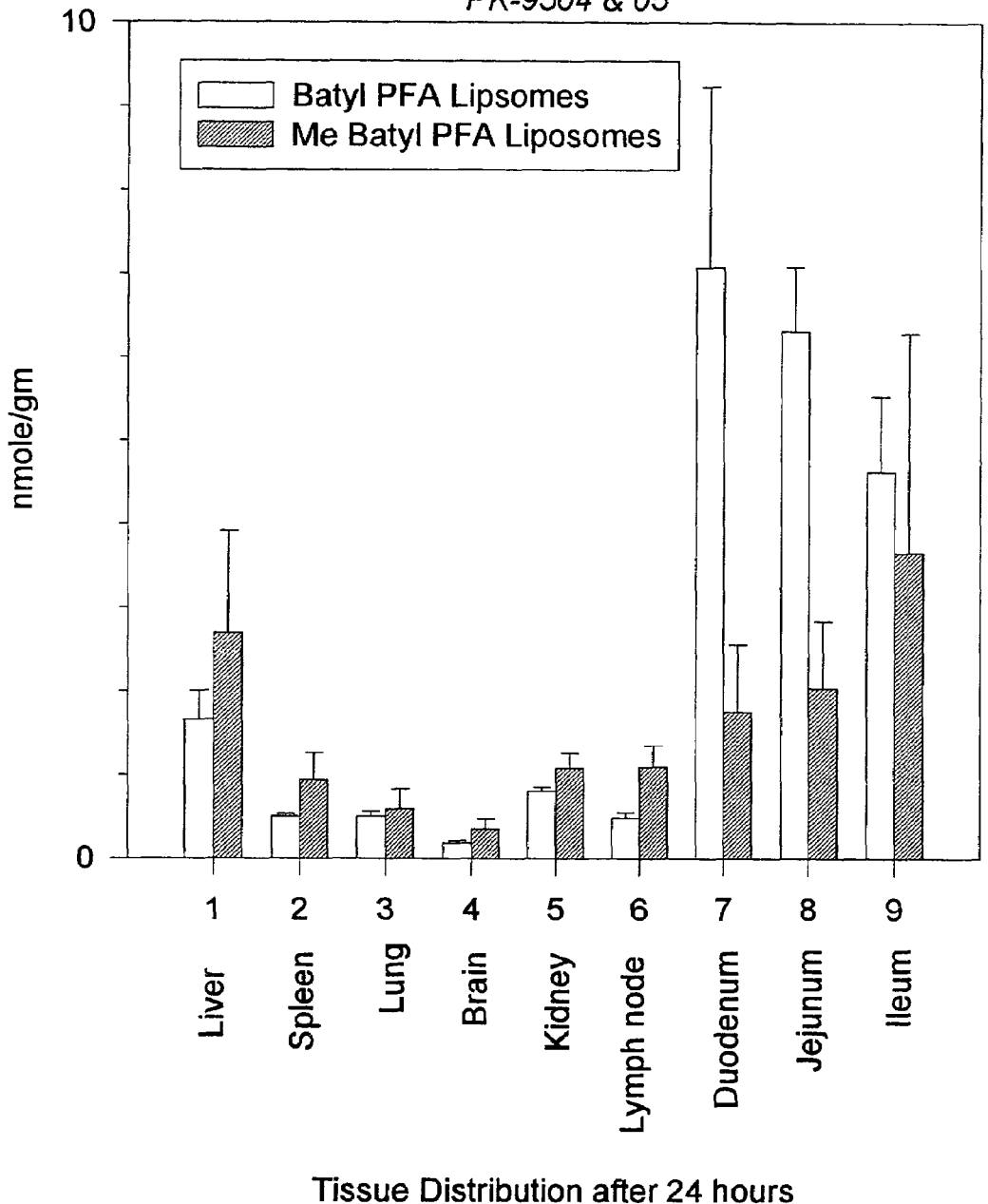
FIG. 2 shows tissue distribution after 24 hours following oral uptake of [$^{14}$C] PFA analogs.

As can be appreciated from FIG. 2, liposomes containing Batyl-PFA (1-O-octadecyl-sn-glycero-3-PFA) provided lower levels of drug in most tissues studied including liver, spleen, jejunum and ileum. However, with the compound of the invention, methylbatyl-PFA (1-O-octadecyl-2-O-methyl-sn-glycero-3-PFA), it was surprisingly observed that drug levels were lower in the small intestine and higher tissue levels of drug were observed in liver, spleen, lung, brain, kidney and lymph node. This suggests that batyl-PFA is not fully delivered to the circulation after its uptake into the small intestinal cells, resulting in lower tissue levels of drug. Conversely, a compound of the invention, Methyl-batyl-PFA [$^{14}$C], is more readily cleaved from the small intestine providing higher levels of drug in liver, lung, kidney, lymph node, spleen and brain. It is anticipated that the other lipid moieties claimed in this invention will also provide similar results.

Furthermore, the benefits arise not from the drug moiety attached to the lipid, but from the lipid moiety itself which enhances small intestinal uptake and tissue penetration shown in FIG. 2.

All publications and patent applications cited in this specification are herein incorporated by reference as if each individual publication or patent application are specifically and individually indicated to be incorporated by reference.

Accordingly, the invention may be embodied in other specific forms without departing from its spirit or essential. characteristics. The described embodiments are to be considered in all respects only as illustrative and tho restrictive, and the scope of the invention is, therefore, indicated by the appended claims rather than by the foregoing description. All modifications which come within the meaning and range of the lawful equivalency of the claims are to be embraced within their scope.

What is claimed is:

1. A method for enhancing oral bioavailability of a drug, comprising linking the drug to a compound having the structure (I):

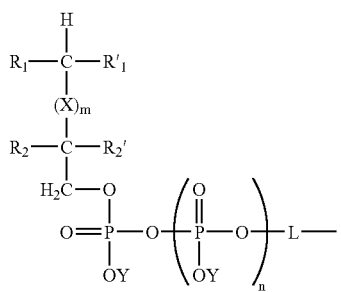

wherein:
$R_1$ and $R_1'$ are independently —H, —O($C_1$ to $C_{24}$)alkyl, —S($C_1$ to $C_{24}$)alkyl, —O($C_2$ to $C_{24}$)alkenyl, —S($C_2$ to $C_{24}$)alkenyl, —CO$_2$($C_1$ to $C_{23}$)alkyl, —OC(O)($C_2$ to $C_{23}$)alkenyl, —OS(O)($C_1$ to $C_{23}$)alkyl, —OS(O)($C_2$ to $C_{23}$)alkenyl; provided that $R_1$ and $R_1'$ are not both —H;
each of $R_2$ and $R_2'$ is —H, or $R_2$—C—$R_2'$ is C=O;
X is CHR$_2$;
m is 0 to 6;
Y is —H; or when said compound is in the form of a salt, each OY is O$^-$A$^+$, wherein each A$^+$ is a physiologically acceptable cation;
n is 1 or 2; and
L is optional and if present, L is a bifunctional linking moiety of the formula J—(CH$_2$)$_t$-G, wherein t is 1 to 24, and wherein each of J and G is independently selected such that the phosphate moiety is bound directly to the terminal methylene of the linker, and
the drug is linked directly to the phosphate moiety of structure (I) or J and G are selected such that the drug is linked indirectly to the phosphate via direct attachment to L via an ester or an amide moiety, thereby enhancing oral bioavailability of the drug.

2. A method for increasing target tissue uptake of a drug, comprising linking the drug to a compound having the structure (I):

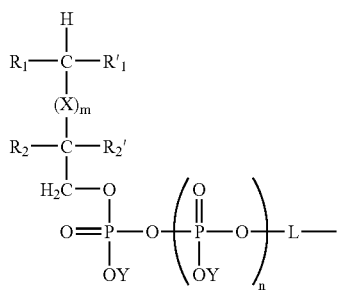

wherein:
$R_1$ and $R_1'$ are independently —H, —O($C_1$ to $C_{24}$)alkyl, —S($C_1$ to $C_{24}$)alkyl, —O($C_2$ to $C_{24}$)alkenyl, —S($C_2$ to $C_{24}$)alkenyl, —CO$_2$($C_1$ to $C_{23}$)alkyl, —OC(O)($C_2$ to $C_{23}$)alkenyl, —OS(O)($C_1$ to $C_{23}$)alkyl, —OS(O)($C_2$ to $C_{23}$)alkenyl; provided that $R_1$ and $R_1'$ are not both —H;
each of $R_2$ and $R_2'$ is —H, or $R_2$—C—$R_2'$ is C=O;
X is CHR$_2$;
m is 0 to 6;
Y is —H; or when said compound is in the form of a salt, each OY is O-A$^+$, wherein each A$^+$ is a physiologically acceptable cation;
n is 1 or 2; and
L is optional and if present, L is a bifunctional linking moiety of the formula J—(CH$_2$)$_t$-G, wherein t is 1 to 24, and wherein each of J and G is independently selected such that the phosphate moiety is bound directly to the terminal methylene of the linker, and
the drug is linked directly to the phosphate moiety of structure (I) or J and G are selected such that the drug is linked indirectly to the phosphate via direct attachment to L via an ester or an amide moiety, thereby increasing target tissue uptake of the drug.

3. A method of enhancing the bioavailability of a molecule, wherein the molecule is unavailable or poorly available in a mammal through oral, intravenous, intramuscular, subcutaneous, parenteral or topical route of administration, wherein the method comprises covalently linking said molecule to a phospholipid species either directly through the phosphate group of the lipid species or indirectly through a bifunctional linking group to form a compound having the structure (I):

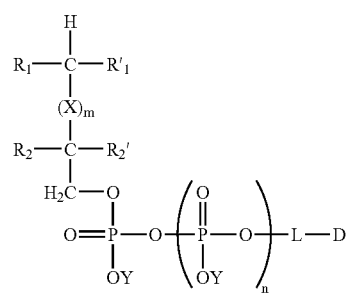

wherein:
$R_1$ and $R_1'$ are independently —H, —O($C_1$ to $C_{24}$)alkyl, —S($C_1$ to $C_{24}$)alkyl, —O($C_2$ to $C_{24}$)alkenyl, —S($C_2$ to $C_{24}$)alkenyl, —CO$_2$($C_1$ to $C_{23}$)alkyl, —OC(O)($C_2$ to $C_{23}$)alkenyl, —OS(O)($C_1$ to $C_{23}$)alkyl, —OS(O)($C_2$ to $C_{23}$)alkenyl; provided that $R_1$ and $R_1'$ are not both —H;
each of $R_2$ and $R_2'$ is —H, or $R_2$—C—$R_2'$ is C=O;
X is CHR$_2$;
m is 0 to 6;
Y is —H; or when said compound is in the form of a salt, each OY is O$^-$A$^+$, wherein each A$^+$ is a physiologically acceptable cation;
n is 1 or 2; and
L is optional and if present, L is a bifunctional linking moiety of the formula J—(CH$_2$)$_t$-G, wherein t is 1 to 24, and wherein each of J and G is independently selected such that the phosphate moiety is bound directly to the terminal methylene of the linker, and
D is a molecule linked directly to the phosphate moiety of structure (I) or J and G are selected such that the drug is linked indirectly to the phosphate via direct attachment to L via an ester or an amide moiety,
thereby improving bioavailability of the molecule.

4. The method of claim 3, wherein D is a molecule having an —OH, —SH, carboxyl, or amino functional group through which it is directly linked to the phosphate group of structure (I) or indirectly linked to the phosphate group of structure (I) if L is present.

5. The method of claim 3 further comprising incorporating the pharmaceutical agent into a therapeutic formulation suitable for oral, intravenous, subcutaneous, parenteral or topical administration.

6. A compound having the structure (II):

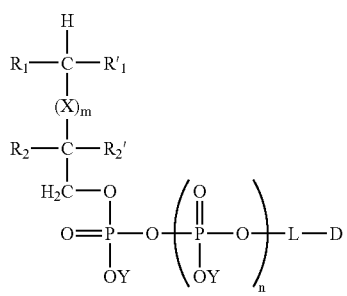

wherein:
R$_1$ and R$_1$' are independently —H, —O(C$_1$ to C$_{24}$)alkyl, —S(C$_1$ to C$_{24}$)alkyl, —O(C$_2$ to C$_{24}$)alkenyl, —S(C$_2$ to C$_{24}$)alkenyl, —CO$_2$(C$_1$ to C$_{23}$)alkyl, —OC(O)(C$_2$ to C$_{23}$)alkenyl, —OS(O)(C$_1$ to C$_{23}$)alkyl, —OS(O)(C$_2$ to C$_{23}$)alkenyl; provided that R$_1$ and R$_1$' are not both —H;
each of R$_2$ and R$_2$' is —H, or R$_2$—C—R$_2$' is C=O;
X is CHR$_2$;
m is 0 to 6;
Y is —H; or when said compound is in the form of a salt, each OY is O$^-$A$^+$, wherein each A$^+$ is a physiologically acceptable cation;
n is 1 or 2; and
L is optional and if present, L is a bifunctional linking moiety of the formula J—(CH$_2$)$_t$-G, wherein t is 1 to 24, and wherein each of J and G is independently selected such that the phosphate moiety is bound directly to the terminal methylene of the linker, and
D is a nucleoside or nucleoside analogue,
wherein the nucleoside or nucleoside analogue possesses anti-viral properties and is suitable for anti-viral therapy, with the further proviso that the nucleoside or nucleoside analogue consists of a first moiety and a second moiety chemically bonded to the first moiety, wherein the first moiety is a substituted or unsubstituted purine or pyrimidine; and the second moiety is an acyclic hydroxylated fragment of a ribose, a ribose deoxypentose.

7. The compound of claim 5, wherein the nucleoside analogue has an acyclic hydroxylated fragment of ribose.

8. The compound of claim 7, wherein the acyclic hydroxylated fragment of ribose is hydroxylated 2-propoxymethyl.

9. The compound of claim 7, wherein the acyclic hydroxylated fragment of ribose is hydroxylated ethoxymethyl.

10. The compound of claim 6, wherein the nucleoside has a ribose.

11. The compound of claim 6, wherein the nucleoside analogue is ganciclovir or acyclovir.

12. The compound of claim 6, wherein substituted purine is phosphonomethoxydiaminopurine.

13. The compound of claim 6, wherein the substituted purine is phosphonomethoxyethyl deoxydiaminopurine.

14. The compound of claim 6, wherein the substituted purine is 9-(2-phosphonylmethoxyethyl)adenine.

15. The compound of claim 6, wherein the substituted purine is 9-(4'-hydroxy-1',2'-butadienyl) adenine.

16. The compound of claim 6, wherein the substituted pyrimidine is 9-(4'-hydroxy-1',2'-butadienyl) cytosine.

17. The compound of claim 6, wherein the substituted pyrimidine is 3-(4'-hydroxy-1',2'-butadienyl) cytosine.

18. The compound of claim 6, wherein the purine or pyrimidine is selected from the group consisting of adenine, guanine, cytosine, and thymine.

19. The compound of claim 18, wherein the pyrimidine is cytosine.

20. The compound of claim 18, wherein the purine is adenine.

21. The compound of claim 18, wherein the pyrimidine is thymine.

22. The compound of claim 18, wherein the purine is guanine.

23. The compound of claim 6, wherein the nucleoside or nucleoside analogue has a 2,6-diaminopurine.

24. A pharmaceutical composition comprising an anti-virally effective amount of a compound of any one of claims 6-10, 11 or 12-23 and a physiologically acceptable carrier.

25. The pharmaceutical composition of claim 24, wherein the physiologically acceptable carrier is suitable for oral delivery.

26. The pharmaceutical composition of claim 24, wherein the physiologically acceptable carrier is suitable for intravenous delivery.

27. The pharmaceutical composition of claim 24, wherein the physiologically acceptable carrier is suitable for intraperitoneal delivery.

28. The pharmaceutical composition of claim 24, wherein the physiologically acceptable carrier is suitable for intramuscular delivery.

29. The pharmaceutical composition of claim 24, wherein the physiologically acceptable carrier is suitable for subcutaneous delivery.

30. The pharmaceutical composition of claim 24, wherein the physiologically acceptable carrier is suitable for topical delivery.

31. A compound having the structure (II):

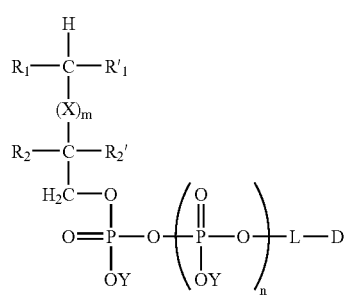

wherein:
R$_1$ and R$_1$' are independently —H, —O(C$_1$ to C$_{24}$)alkyl, —S(C$_1$ to C$_{24}$)alkyl, —O(C$_2$ to C$_{24}$)alkenyl, —S(C$_2$ to C$_{24}$)alkenyl, —CO$_2$(C$_1$ to C$_{23}$)alkyl, —OC(O)(C$_2$ to $C_{23}$)alkenyl, —OS(O)($C_1$ to $C_{23}$)alkyl, —OS(O)($C_2$ to $C_{23}$)alkenyl; provided that $R_1$ and $R_1'$ are not both —H;

each of $R_2$ and $R_2'$ is —H, or $R_2$—C—$R_2'$ is C=O;

X is $CHR_2$;

m is 0 to 6;

Y is —H; or when said compound is in the form of a salt, each OY is $O^-A^+$, wherein each $A^+$ is a physiologically acceptable cation;

n is 1 or 2; and

L is optional and if present, L is a bifunctional linking moiety of the formula J—$(CH_2)_t$-G, wherein t is 1 to 24, and wherein each of J and G is independently selected t such that the phosphate moiety is bound directly to the terminal methylene of the linker, and D is a nucleoside or nucleoside analogue, wherein the nucleoside or nucleoside analogue possesses anti-viral properties and is suitable for anti-viral therapy, wherein the antiviral nucleoside or nucleoside analogue comprises an acyclic hydroxylated fragment of a ribose, a ribose, or deoxypentose.

32. The compound of claim 31 wherein the nucleoside analogue is acyclovir.

33. The compound of claim 31 wherein the nucleoside analogue is ganciclovir.

34. A compound having the structure (II):

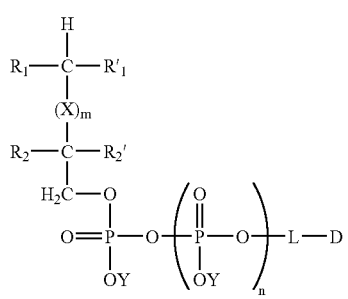

II wherein:

$R_1$ and $R_1'$ are independently —H, —O($C_1$ to $C_{24}$)alkyl, —S($C_1$ to $C_{24}$)alkyl, —O($C_2$ to $C_{24}$)alkenyl, —S($C_2$ to $C_{24}$)alkenyl, —$CO_2$($C_1$ to $C_{23}$)alkyl, —OC(O)($C_2$ to $C_{23}$)alkenyl, —OS(O)($C_1$ to $C_{23}$)alkyl, —OS(O)($C_2$ to $C_{23}$)alkenyl; provided that $R_1$ and $R_1'$ are not both —H;

each of $R_2$ and $R_2'$ is —H, or $R_2$—C—$R_2'$ is C=O;

X is $CHR_2$;

m is 0 to 6;

Y is —H; or when said compound is in the form of a salt, each OY is $O^-A^+$, wherein each $A^+$ is a physiologically acceptable cation;

n is 1 or 2; and

L is optional and if present, L is a bifunctional linking moiety of the formula J—$(CH_2)_t$-G, wherein t is 1 to 24, and wherein each of J and G is independently selected such that the phosphate moiety is bound directly to the terminal methylene of the linker, and D is a nucleoside or nucleoside analogue, wherein the nucleoside or nucleoside analogue possesses anti-viral properties and is suitable for anti-viral therapy, with the further proviso that the nucleoside or nucleoside analogue has:

(a) a substituted or unsubstituted purine or pyrimidine selected from the group consisting of adenine, thymine, cytosine, guanine, 2,6-diaminopurine, 6-oxypurine, and 8-azaguanine; and (b) a 2'-deoxyribose.

35. A pharmaceutical composition comprising an anti-virally effective amount of a compound of claim 34 and a physiologically acceptable carrier.

* * * * *